(12) United States Patent
Harden et al.

(10) Patent No.: US 12,178,811 B2
(45) Date of Patent: Dec. 31, 2024

(54) METHODS OF TREATING DEPRESSIVE DISORDERS

(71) Applicant: Xenon Pharmaceuticals Inc., Burnaby (CA)

(72) Inventors: Cynthia Louise Harden, Burnaby (CA); Gregory N. Beatch, Burnaby (CA)

(73) Assignee: Xenon Pharmaceuticals Inc., Burnaby (CA)

( * ) Notice: Subject to any disclaimer, the term of this patent is extended or adjusted under 35 U.S.C. 154(b) by 162 days.

(21) Appl. No.: 17/093,183

(22) Filed: Nov. 9, 2020

(65) Prior Publication Data

US 2021/0161886 A1   Jun. 3, 2021

Related U.S. Application Data

(60) Provisional application No. 62/932,724, filed on Nov. 8, 2019.

(51) Int. Cl.
*A61K 31/472* (2006.01)
*A61K 9/00* (2006.01)
*A61P 25/24* (2006.01)

(52) U.S. Cl.
CPC .......... *A61K 31/472* (2013.01); *A61K 9/0053* (2013.01); *A61P 25/24* (2018.01)

(58) Field of Classification Search
CPC ............................... A61K 31/472; A61P 25/24
See application file for complete search history.

(56) References Cited

U.S. PATENT DOCUMENTS

| | | | |
|---|---|---|---|
| 3,639,385 | A | 2/1972 | Weaver et al. |
| 3,845,770 | A | 11/1974 | Theeuwes et al. |
| 4,181,803 | A | 1/1980 | Morita et al. |
| 4,326,525 | A | 4/1982 | Swanson et al. |
| 4,554,281 | A | 11/1985 | vonBebenburg et al. |
| 4,668,684 | A | 5/1987 | Tibes et al. |
| 4,778,799 | A | 10/1988 | Tibes et al. |
| 4,923,858 | A | 5/1990 | Engel et al. |
| 4,923,974 | A | 5/1990 | Ueda et al. |
| 5,032,591 | A | 7/1991 | Evans et al. |
| 5,162,346 | A | 11/1992 | Lobisch et al. |

(Continued)

FOREIGN PATENT DOCUMENTS

| | | |
|---|---|---|
| CA | 2542434 A1 | 5/2005 |
| DE | 3337593 A1 | 5/1984 |

(Continued)

OTHER PUBLICATIONS

Can et al., "The Mouse Forced Swim Test," J. Vis. Exp. (59), e3638, DOI:10.3791/3638 (2012).

(Continued)

*Primary Examiner* — San Ming R Hui
(74) *Attorney, Agent, or Firm* — Wolf, Greenfield & Sacks, P.C.

(57) ABSTRACT

In certain embodiments, the present disclosure is directed to methods for treating depressive disorders in a human, wherein the methods comprise orally administering a therapeutically effective amount of N-[4-(6-fluoro-3,4-dihydro-1H-isoquinolin-2-yl)-2,6-dimethylphenyl]-3,3-dimethylbutanamide (Compound A), to the human in need thereof. The present disclosure is further directed to various improved methods of therapy and administration of Compound A.

21 Claims, 3 Drawing Sheets

(56) References Cited

U.S. PATENT DOCUMENTS

| | | |
|---|---|---|
| 5,234,947 A | 8/1993 | Cherksey |
| 5,262,419 A | 11/1993 | Aberg et al. |
| 5,284,861 A | 2/1994 | Lobisch et al. |
| 5,384,330 A | 1/1995 | Dieter et al. |
| 5,428,039 A | 6/1995 | Cohen |
| 5,502,058 A | 3/1996 | Mayer et al. |
| 5,643,921 A | 10/1997 | Grover |
| 5,679,706 A | 10/1997 | D'Alonzo et al. |
| 5,760,007 A | 6/1998 | Shank |
| 5,800,385 A | 9/1998 | Demopulos et al. |
| 5,849,789 A | 12/1998 | Rostock et al. |
| 5,852,053 A | 12/1998 | Rostock et al. |
| 5,858,017 A | 1/1999 | Demopulos et al. |
| 5,860,950 A | 1/1999 | Demopulos et al. |
| 5,914,425 A | 6/1999 | Meisel et al. |
| 5,925,634 A | 7/1999 | Olney |
| 6,117,900 A | 9/2000 | Rundfeldt et al. |
| 6,211,171 B1 | 4/2001 | Sawynok et al. |
| 6,218,411 B1 | 7/2001 | Koga |
| 6,281,211 B1 | 8/2001 | Cai et al. |
| 6,265,417 B1 | 12/2001 | Carroll |
| 6,326,385 B1 | 12/2001 | Wickenden et al. |
| 6,348,486 B1 | 2/2002 | Argentieri et al. |
| 6,395,736 B1 | 5/2002 | Parks et al. |
| 6,451,857 B1 | 9/2002 | Hurtt et al. |
| 6,469,042 B1 | 10/2002 | Hewawasam et al. |
| 6,472,165 B1 | 10/2002 | Rundfeldt et al. |
| 6,495,550 B2 | 12/2002 | McNaughton-Smith et al. |
| 6,500,455 B1 | 12/2002 | Frantsits |
| 6,537,991 B1 | 3/2003 | Shaw et al. |
| 6,538,004 B2 | 3/2003 | Drizin |
| 6,538,151 B1 | 3/2003 | Meisel et al. |
| RE38,115 E | 5/2003 | Smith et al. |
| 6,589,986 B2 | 7/2003 | Bowlby et al. |
| 6,593,335 B1 | 7/2003 | Carroll |
| 6,642,209 B1 | 11/2003 | Fukunuga |
| 6,645,521 B2 | 11/2003 | Cassel |
| 6,737,422 B2 | 5/2004 | McNaughton-Smith et al. |
| 7,045,551 B2 | 5/2006 | Wu et al. |
| 7,160,684 B2 | 1/2007 | Argentieri et al. |
| 7,250,511 B2 | 7/2007 | Bavetsias |
| 7,309,713 B2 | 12/2007 | Rundfeldt et al. |
| 7,419,981 B2 | 9/2008 | Field et al. |
| 8,119,602 B2 | 2/2012 | Zhang et al. |
| 8,236,861 B2 | 8/2012 | Anttila |
| 8,293,911 B2 | 10/2012 | Vernier et al. |
| 8,993,593 B2 | 3/2015 | Vernier et al. |
| 11,091,441 B2 | 8/2021 | Bichler et al. |
| 11,135,214 B2 | 10/2021 | Beatch |
| 2002/0013349 A1 | 1/2002 | Wickenden |
| 2002/0015730 A1 | 2/2002 | Hoffmann et al. |
| 2002/0183395 A1 | 12/2002 | Argentieri |
| 2004/0198724 A1 | 10/2004 | McNaughton-Smith |
| 2005/0070570 A1 | 3/2005 | Garcia et al. |
| 2005/0089473 A1 | 4/2005 | Black et al. |
| 2005/0089559 A1 | 4/2005 | Szelenyi |
| 2005/0090547 A1 | 4/2005 | Szelenyi |
| 2005/0202394 A1 | 9/2005 | Dobson |
| 2005/0277579 A1 | 12/2005 | Krishnan et al. |
| 2007/0066612 A1 | 3/2007 | Khanzhin et al. |
| 2008/0139610 A1 | 6/2008 | Vernier et al. |
| 2009/0018154 A1 | 1/2009 | Kao et al. |
| 2009/0318507 A2 | 12/2009 | Rundfeldt et al. |
| 2010/0256145 A1 | 10/2010 | Bak-Jensen et al. |
| 2011/0003850 A1 | 1/2011 | Vernier et al. |
| 2013/0131030 A1 | 5/2013 | Belanoff et al. |
| 2014/0148478 A1 | 5/2014 | Kühnert et al. |
| 2019/0343823 A1 | 11/2019 | Beatch |
| 2021/0213009 A1 | 7/2021 | Johnson et al. |
| 2022/0062266 A1 | 3/2022 | Beatch |
| 2022/0064120 A1 | 3/2022 | Bichler |
| 2022/0265634 A1 | 8/2022 | Pimstone |
| 2022/0288057 A1 | 9/2022 | Johnson |
| 2023/0015539 A1 | 1/2023 | Murrough et al. |

FOREIGN PATENT DOCUMENTS

| | | |
|---|---|---|
| DE | 3604575 A1 | 8/1986 |
| DE | 10359335 A1 | 5/2005 |
| EP | 0189788 A1 | 8/1986 |
| EP | 1334972 A1 | 8/2003 |
| EP | 1407768 A2 | 4/2004 |
| EP | 1813285 A1 | 8/2007 |
| EP | 4074696 A1 | 10/2022 |
| JP | 2000-014350 A | 5/2000 |
| JP | 2013-517315 A | 5/2013 |
| JP | 2013-518043 A | 5/2013 |
| WO | 00/55137 A1 | 9/2000 |
| WO | 00/59487 A2 | 10/2000 |
| WO | 00/59508 A1 | 10/2000 |
| WO | 01/001970 A2 | 1/2001 |
| WO | 01/01972 A2 | 1/2001 |
| WO | 01/009612 A1 | 2/2001 |
| WO | 01/22953 A2 | 4/2001 |
| WO | 02/080898 A2 | 10/2002 |
| WO | 03/020706 A1 | 3/2003 |
| WO | 03/097586 A1 | 11/2003 |
| WO | 03/106454 A1 | 12/2003 |
| WO | 04/082677 A1 | 3/2004 |
| WO | 04/058739 A1 | 7/2004 |
| WO | 04/080950 A1 | 9/2004 |
| WO | 2004/096767 A1 | 11/2004 |
| WO | 04/105795 A1 | 12/2004 |
| WO | 05/087754 A1 | 3/2005 |
| WO | 2005/039576 A1 | 5/2005 |
| WO | 05/048975 A1 | 6/2005 |
| WO | 05/100349 A2 | 10/2005 |
| WO | 06/029623 A1 | 3/2006 |
| WO | 06/092143 A1 | 9/2006 |
| WO | 2008-024398 A1 | 2/2008 |
| WO | 08/066900 A1 | 6/2008 |
| WO | WO 2011/089126 A2 | 7/2011 |
| WO | WO 2011/090923 A1 | 7/2011 |
| WO | 2013/067591 A1 | 5/2013 |
| WO | WO 2019/217924 A1 | 11/2019 |
| WO | WO 2021/092439 A1 | 5/2021 |
| WO | WO 2021/113802 A1 | 6/2021 |

OTHER PUBLICATIONS

Friedman et al., "KCNQ channel openers reverse depressive symptoms via an active resilience mechanism," Nature Communications, 7:11671, 2016.

International Search Report and Written Opinion corresponding to International Application No. PCT/US2020/059481 dated Feb. 22, 2021.

Tan et al., "Effects of the KCNQ channel opener ezogabine on functional connectivity of the ventral striatum and clinical symptoms in patients with major depressive disorder," Molecular Psychiatry (2020) 25:1323-1333.

International Preliminary Report on Patentability, dated May 19, 2022 for International Application No. PCT/US2020/059481.

PCT/US2020/059481, May 19, 2022, International Preliminary Report on Patentability.

Enna et al., The GABA Receptors. In: Enna and Möhler, The GABA Receptors, Third Edition. 2007. Humana Press Inc, Totawa, NJ. 26 pages.

Greenfield, L.J., Molecular mechanisms of antiseizure drug activity at GABAA receptors. Seizure. 2013; 22(8):589-600. doi: 10.1016/j.seizure.2013.04.015.

Luscher et al., The GABAergic deficit hypothesis of major depressive disorder. Mol Psychiatry. 2011; 16(4):383-406. doi: 10.1038/mp.2010.120.

Treven et al., The anticonvulsant retigabine is a subtype selective modulator of GABAA receptors. Epilepsia. 2015; 56(4):647-57. doi: 10.1111/epi.12950.

[No Author Listed], NCT03796962: A Study to Evaluate XEN1101 as Adjunctive Therapy in Focal Epilepsy. Last Update Posted Nov. 1, 2021. 12 pages. Accessed May 17, 2022 from <https://clinicaltrials.gov/ct2/show/NCT03796962>.

(56) References Cited

OTHER PUBLICATIONS

[No Author Listed], Potiga (ezogabine) Tablets, CV. FDA Approved Labeling (2012) NDA 022345/S-001. 21 pages.

[No Author Listed], Submission PM-2011-04248-3-1. Extract from the Clinical Evaluation Report for Retigabine. Australian Government Department of Health. (Jul. 9, 2012) pp. 1-89.

[No Author Listed], Xenon Pharmaceuticals Announces Initiation of XEN1101 Phase 1 Clinical Trial. Xenon Pharmaceuticals Inc. (Oct. 17, 2017) Accessed from <https://investor.xenon-pharma.com/news-releases/news-release-details/xenon-pharmaceuticals-announces-initiation-xen1101-phase-1>. 4 pages.

Aycardi et al., A First-in-Human Study to Assess the Safety, Tolerability, Pharmacokinetics and Preliminary Pharmacodynamics of a Novel Small Molecule KV7.2/7.3 Positive Allosteric Modulator (XEN1101) in Healthy Subjects. Presented at the 72nd Annual Meeting of the American Epilepsy Society, New Orleans, LA (Nov. 30-Dec. 4, 2018). 1 page. Poster.

Aycardi, E., $K_v7$ Potassium Channel Modulators for the Treatment of Epilepsy. Xenon Pharmaceuticals Inc. Presented at the 2020 Epilepsy Foundation Pipline Conference. (Aug. 27, 2020) 14 pages.

Beatch et al., A Phase 1 Study Utilizing Transcranial Magnetic Stimulation to Assess the Pharmacodynamic Effects of a Novel Potassium Channel Opener (XEN1101) on Human Cortical Excitability. Presented at the 72nd Annual Meeting of the American Epilepsy Society, New Orleans, LA (Dec. 3, 2018). 1 page. Poster.

Beatch et al., Use of Transcranial Magnetic Stimulation Data in the Design of a Dose Ranging Finding Efficacy, Safety, Tolerability and Pharmacokinetics Study of XEN1101 in Patients with Focal Epilepsy. Xenon Pharmaceuticals Inc. 73rd Annual Meeting of the American Epilepsy Society in Baltimore, MD. Dec. 6-10, 2019. Poster. 1 page. Accessed from <https://www.xenon-pharma.com/wp-content/uploads/2019/12/Beatch_Poster_72x42-FINALi.pdf>. Last accessed May 17, 2022.

Beck et al. An inventory for measuring clinical anxiety: psychometric properties. J Consult Clin Psychol. (1988) 56(6): 893-897.

Bialer et al., Progress report on new antiepileptic drugs: A summary of the Thirteenth EILAT Conference on New Antiepileptic Drugs and Devices (EILAT XIII). Epilepsia. (Feb. 2017) 58(2):181-221. doi: 10.1111/epi.13634.

Bialer et al., Progress report on new antiepileptic drugs: A summary of the Fourteenth EILAT Conference on New Antiepileptic Drugs and Devices (EILAT XIV). I. Drugs in preclinical and early clinical development. Epilepsia. (Oct. 2018) 59(10):1811-1841. doi: 10.1111/epi.14557.

Bialer et al., Progress report on new antiepileptic drugs: A summary of the Fifteenth Eilat Conference on New Antiepileptic Drugs and Devices (EILAT XV). I. Drugs in preclinical and early clinical development. Epilepsia. Nov. 2020;61(11):2340-2364. doi: 10.1111/epi.16725. Epub Nov. 14, 2020.

Borgini et al., Chemical modulation of Kv7 potassium channels. RSC Med Chem. (Jan. 14, 2021) 12(4):483-537. doi: 10.1039/d0md00328j.

Brown et al., Muscarinic suppression of a novel voltage-sensitive $K^+$ current in a vertebrate neurone. Nature. (Feb. 14, 1980) 283(5748):673-676. doi: 10.1038/283673a0.

Carlisle et al., Estimation of total hepatic blood flow by duplex ultrasound. Gut. (Jan. 1992) 33(1):92-97. doi: 10.1136/gut.33.1.92.

Cheng et al., Food Effects on Oral Drug Absorption: Application of Physiologically-Based Pharmacokinetic Modeling as a Predictive Tool. Pharmaceutics. (Jul. 17, 2020) 12(7):672. doi: 10.3390/pharmaceutics12070672.

Duru et al., The clinical relevance of changes in the Montgomery-Asberg Depression Rating Scale using the minimum clinically important difference approach. Curr Med Res Opin. (2008) 24(5):1329-1335.

Goldberg, Y.P., XEN1101, a Novel Modulator of Kv7.2/3 for the Treatment of Epilepsy. Presented at The Epilepsy Foundation Pipeline Conference, San Francisco, CA (Feb. 22-23, 2018) 10 pages.

Goldberg, Y.P., XEN1101: A Novel, Next-Generation KCNQ2 Modulator for the Treatment of Epilepsy. Presented at the EILAT XIV Meeting, Madrid, Spain (May 15, 2018) 32 pages.

Hamilton, M., A rating scale for depression. J Neurol Neurosurg Psychiatry. (Feb. 1960) 23(1):56-62. doi: 10.1136/jnnp.23.1.56.

Harmer et al., How do antidepressants work? New perspectives for refining future treatment approaches. Lancet Psychiatry. (May 2017) 4(5):409-418. doi: 10.1016/S2215-0366(17)30015-9.

Harris et al., Retigabine (ezogabine) as add-on therapy for partial-onset seizures: an update for clinicians. Ther Adv Chronic Dis. (Nov. 2011) 2(6):371-376. doi: 10.1177/2040622311421542.

Heimbach et al., Case studies for practical food effect assessments across BCS/BDDCS class compounds using in silico, in vitro, and preclinical in vivo data. Aaps J. (Jan. 2013) 15(1):143-158. doi: 10.1208/s12248-012-9419-5.

Hino et al., Drug Interaction, 34. Drug Interactions of food and medicine. J Okayama Med Assoc. (Dec. 1, 2015) 127(3):245-249. doi: 10.4044/joma.127.245.

Hirtz et al., How common are the "common" neurologic disorders? Neurology. (Jan. 30, 2007) 68(5):326-337. doi: 10.1212/01.wnl.0000252807.38124.a3.

Hitiris et al., Mortality in epilepsy. Epilepsy Behav. (May 2007) 10(3):363-376. doi: 10.1016/j.yebeh.2007.01.005.

Johannessen et al., Management of focal-onset seizures: an update on drug treatment. Drugs. (2006) 66(13):1701-1725. doi: 10.2165/00003495-200666130-00004.

Kupferberg, H., Antiepileptic drug development program: a cooperative effort of government and industry. Epilepsia. (1989) 30 Suppl 1:S51-S56; discussion S64-S68. doi: 10.1111/j.1528-1157.1989.tb05815.x.

Lang et al., Effects of lacosamide and carbamazepine on human motor cortex excitability: a double-blind, placebo-controlled transcranial magnetic stimulation study. Seizure. (Nov. 2013) 22(9):726-730. doi: 10.1016/j.seizure.2013.05.010.

Maguire, J., Neuroactive Steroids and GABAergic Involvement in the Neuroendocrine Dysfunction Associated With Major Depressive Disorder and Postpartum Depression. Front Cell Neurosci. (Mar. 8, 2019) 13:83. doi: 10.3389/fncel.2019.00083.

Marvanova, M., Pharmacokinetic characteristics of antiepileptic drugs (AEDs). Ment Health Clin. (Mar. 8, 2016) 6(1):8-20. doi: 10.9740/mhc.2015.01.008.

Marzo et al., Pharmacokinetics and pharmacodynamics of safinamide, a neuroprotectant with antiparkinsonian and anticonvulsant activity. Pharmacol Res. (Jul. 2004) 50(1):77-85. doi: 10.1016/j.phrs.2003.12.004.

Montgomery et al., A new depression scale designed to be sensitive to change. Br J Psychiatry. (Apr. 1979) 134:382-389. doi: 10.1192/bjp.134.4.382.

Ossemann et al., Effect of a single dose of retigabine in cortical excitability parameters: A cross-over, double-blind placebo-controlled TMS study. Epilepsy Res. (Oct. 2016) 126:78-82. doi: 10.1016/j.eplepsyres.2016.06.004.

Pimstone, S., New Anti-Epileptic Drugs and Devices. Xenon Pharmaceuticals Inc. Presented at the EILAT XV Conference. (Jul. 27-30, 2020) 24 pages.

Pithavala et al., Evaluation of the effect of food on the pharmacokinetics of axitinib in healthy volunteers. Cancer Chemother Pharmacol. (Jul. 2012) 70(1):103-112. doi: 10.1007/s00280-012-1888-9.

Premoli, I., A First-in-Human Phase I Study to Assess the Pharmacodynamic Profile of a Novel Potassium Channel Opener (XEN1101) on Human Cortical Excitability with TMS-EEG and TMS-EMG. Presented at the 13th European Congress on Epileptology. King's College London Institute of Psychiatry, Psychology and Neuroscience. (Aug. 29, 2018) 15 pages.

Premoli et al., Lamotrigine and levetiracetam exert a similar modulation of TMS-evoked EEG potentials. Epilepsia. (Jan. 2017) 58(1):42-50. doi: 10.1111/epi.13599.

Premoli et al., TMS as a pharmacodynamic indicator of cortical activity of a novel anti-epileptic drug, XEN1101. Ann Clin Transl Neurol. (Nov. 2019) 6(11):2164-2174. doi: 10.1002/acn3.50896.

Welling, P.G., Effects of food on drug absorption. Annu Rev Nutr. (1996) 16:383-415. doi: 10.1146/annurev.nu.16.070196.002123.

*U.S. Appl. No. 17/449,785, filed Oct. 1, 2021, Beatch.

(56) References Cited

OTHER PUBLICATIONS

*U.S. Appl. No. 18/648,049, filed Apr. 26, 2024, Beatch.
*U.S. Appl. No. 18/679,045, filed May 30, 2024, Beatch.
*U.S. Appl. No. 18/603,554, filed Mar. 13, 2024, Johnson.
*U.S. Appl. No. 18/540,582, filed Dec. 14, 2023, Bichler.
*U.S. Appl. No. 18/415,139, filed Jan. 17, 2024, Johnson et al.
*U.S. Appl. No. 18/604,727, filed Mar. 14, 2024, Pimstone.
[No Author Listed], Depression Assessment Instruments. American Psychological Association. Aug. 2019, last updated Jan. 2023. Accessed at: https://www.apa.org/depression-guideline/assessment. Last accessed: Jun. 20, 2024. 19 pages.
[No Author Listed], Depression in Children. Cleveland Clinic. Last reviewed Nov. 2023. Last Accessed: Jun. 2024. Accessed at: https://my.clevelandclinic.org/ health/diseases/14938-depression-in-children. 9 pages.
[No Author Listed], Grooved Pegboard: Model 32025 User's Manual [Internet]. Lafayette Instrument. 2023. 15 pages.
[No Author Listed], Guidance for Industry: Assessment of Abuse Potential of Drugs. Food and Drug Administration. (Jan. 2017) Accessed from <https://www.fda.gov/regulatory-information/search-fda-guidance-documents/assessment-abuse-potential-drugs>. 37 pages.
[No Author Listed], Guidance for Industry: Environmental Assessment of Human Drug and Biologics Applications. Food and Drug Administration. (Jul. 1998) Accessed from <https://www.fda.gov/media/70809/download>. 42 pages.
[No Author Listed], Guideline on clinical investigation of medicinal products in the treatment of epileptic disorders. European Medicines Agency. Oct. 30, 2023. Available from: https://www.ema.europa.eu/en/documents/scientific-guideline/draft-guideline-clinical-investigation-medicinal-products-treatment-epileptic-disorders-revision-3_en.pdf. Last Accessed Jun. 20, 2024.
[No Author Listed], Guideline on the Environmental Risk Assessment of Medicinal Products for Human Use. European Medicines Agency. (Jun. 1, 2006) Accessed from <https://www.ema.europa.eu/en/documents/scientific-guideline/guideline-environmental-risk-assessment-medicinal-products-human-use-first-version_en.pdf>. 12 pages.
[No Author Listed], Potiga (ezogabine) Tablets Full Prescribing Information. United States Food and Drug Administration. Last revised Jun. 2011. 27 pages.
[No Author Listed], Xenon—Corporate Overview. Jan. 2023; 30 pages. Retrieved from the Internet: URL: https://investor.xenonpharma.com/staticfiles/6420366d-bf5e-4141-a306-a585f818094b.
[No Author Listed], X-Nova Topline Results in Major Depressive Disorder. Xenon Pharmaceuticals Inc. Presented Nov. 27, 2023. 16 pages.
[No Author Listed], Guidance for Industry: Major Depressive Disorder: Developing Drugs for Treatment. Food and Drug Administration. (Jun. 2018) Accessed from <www.fda.gov/media/113988/download>. 11 pages.
Aaberg et al., Seizures, syndromes, and etiologies in childhood epilepsy: The International League Against Epilepsy 1981, 1989, and 2017 classifications used in a population-based cohort. Epilepsia. Nov. 2017;58(11):1880-1891. doi: 10.1111/epi.13913. Epub Sep. 26, 2017.
Aeby et al., Treatment of Focal-Onset Seizures in Children: Should This Be More Etiology-Driven? Front Neurol. Mar. 7, 2022:13:842276. doi: 10.3389/fneur.2022.842276. eCollection 2022.
Andreev et al., Analgesic Activity of Acid-Sensing Ion Channel 3 (ASIC3) Inhibitors: Sea Anemones Peptides Ugr9-1 and APETx2 versus Low Molecular Weight Compounds. Mar Drugs. (Dec. 12, 2018) 16(12):500. doi: 10.3390/md16120500.
Armand et al., Effects of retigabine (D-23129) on different patterns of epileptiform activity induced by 4-aminopyridine in rat entorhinal cortex hippocampal slices. Naunyn-Schmiedebera's Arch Pharmacol. Jan. 1999;359(1):33-9. doi: 10.1007/p100005320.
Armijo et al., Ion channels and epilepsy. Curr Pharm Des. 2005;11(15):1975-2003. doi: 10.2174/1381612054021006.

Barhanin et al., KvLQT1 and ISK (minK) proteins associate to form the IKs cardiac potassium current. Nature. Nov. 7, 1996;384(6604):78-80. doi: 10.1038/384078a0.
Barker et al., Clinical evaluation of conduction time measurements in central motor pathways using magnetic stimulation of human brain. Lancet. Jun. 7, 1986;1(8493):1325-6. doi: 10.1016/s0140-6736(86)91243-2.
Barry et al., The American Urological Association symptom index for benign prostatic hyperplasia. The Measurement Committee of the American Urological Association. J Urol. Nov. 1992; 148(5): 1549-57; discussion 1564. doi: 10.1016/s0022-5347(17)36966-5.
Beck et al., Comparison of Beck Depression Inventories -IA and -II in psychiatric outpatients. J Pers Assess. Dec. 1996;67(3):588-97. doi: 10.1207/s15327752jpa6703_13.
Beeby et al., The synthesis and properties of 2:7-Disubstituted 1:2:3:4-tetrahydroisoquinolines. J Chem Soc. 1949; 385:1799-1803.
Berge et al., Pharmaceutical salts. J Pharm Sci. Jan. 1977;66(1):1-19. doi: 10.1002/jps.2600660104.
Berton et al., Essential role of BDNF in the mesolimbic dopamine pathway in social defeat stress. Science. (Feb. 10, 2006) 311(5762):864-868. doi: 10.1126/science.1120972.
Bharmal et al., Validation of an abbreviated Treatment Satisfaction Questionnaire for Medication (TSQM-9) among patients on antihypertensive medications. Health Qual Life Outcomes. Apr. 27, 2009:7:36. doi: 10.1186/1477-7525-7-36.
Bi et al., Visceral hyperalgesia induced by forebrain-specific suppression of native Kv7/KCNQ/M-current in mice. Mol Pain. (Oct. 26, 2011) 7:84. doi: 10.1186/1744-8069-7-84.
Bialer et al., Progress report on new antiepileptic drugs: a summary of the fourth Eilat conference (EILAT IV). Epilepsy Res. Mar. 1999;34(1):1-41. doi: 10.1016/s0920-1211(98)00108-9.
Bialer, Progress report on new antiepileptic drugs: a summary of the Seventh Eilat Conference (EILAT VII). Epilepsy Res. Sep.-Oct. 2004;61(1-3):1-48. doi: 10.1016/j.eplepsyres.2004.07.010.
Bialer, Progress report on new antiepileptic drugs: a summary of the Sixth Eilat Conference (EILAT VI). Epilepsy Res. Sep. 2002;51(1-2):31-71. doi: 10.1016/s0920-1211(02)00106-7.
Biervert et al., A potassium channel mutation in neonatal human epilepsy. Science. Jan. 16, 1998;279(5349):403-6. doi: 10.1126/science.279.5349.403.
Blackburn-Munro et al., The anticonvulsant retigabine attenuates nociceptive behaviours in rat models of persistent and neuropathic pain. Eur J Pharmacol. (Jan. 24, 2003) 460(2-3):109-116. doi: 10.1016/s0014-2999(02)02924-2.
Boylan et al. Depression but not seizure frequency predicts quality of life in treatment-resistant epilepsy. Neurology. Jan. 27, 2004;62(2):258-61. doi: 10.1212/01.wnl.0000103282.62353.85.
Braatz et al., Particle Size and Shape Control in Crystallization Processes. 2002; 307-327. Accessed at: https://folk.ntnu.no/skoge/prost/proceedings/cpc6-jan 2002/braatz.pdf.
Brodie et al., Antiepileptic drug therapy: does mechanism of action matter? Epilepsy Behav. Aug. 2011;21(4):331-41. doi: 10.1016/j.yebeh.2011.05.025. Epub Jul. 16, 2011.
Brown et al., Muscarinic suppression of a novel voltage-sensitive K+ current in a vertebrate neurone. Nature. Feb. 14, 1980;283(5748):673-6. doi: 10.1038/283673a0.
Brown, Ion Channels. Plenum Press, Eds. 1988. pp. 55-94.
Byrn et al., Pharmaceutical solids: a strategic approach to regulatory considerations. Pharm Res. (Jul. 1995) 12(7):945-954. doi: 10.1023/a:1016241927429.
Cains, P.W., Classical Methods of Preparation of Polymorphs and Alternative Solid Forms. In: Polymorphism in Pharmaceutical Solids. Chapter 4. Second Edition. Brittain, Ed. (2009) pp. 76-138.
Caira, M., Crystalline Polymorphism of Organic Compounds. Top Curr Chem. (Feb. 26, 1999) 198;163-208. doi: 10.1007/3-540-69178-2_5.
Casaca-Carreira et al., Transependymal Cerebrospinal Fluid Flow: Opportunity for Drug Delivery? Mol Neurobiol. (Apr. 2018) 55(4):2780-2788. doi: 10.1007/s12035-017-0501-y. Epub Apr. 28, 2017.
Charlier et al., A pore mutation in a novel KQT-like potassium channel gene in an idiopathic epilepsy family. Nat Genet. Jan. 1998;18(1):53-5. doi: 10.1038/ng0198-53.

(56) References Cited

OTHER PUBLICATIONS

Chaudhury et al., Rapid regulation of depression-related behaviours by control of midbrain dopamine neurons. Nature. (Jan. 24, 2013) 493(7433):532-536. doi: 10.1038/nature11713.
Chen et al., Treatment Outcomes in Patients With Newly Diagnosed Epilepsy Treated With Established and New Antiepileptic Drugs: A 30-Year Longitudinal Cohort Study. JAMA Neurol. Mar. 1, 2018;75(3):279-286. doi: 10.1001/jamaneurol.2017.3949.
Chiesa et al., A systematic review of neurobiological and clinical features of mindfulness meditations. Psychol Med. (Aug. 2010) 40(8):1239-1252. doi: 10.1017/S0033291709991747.
Chourbaji et al., Learned helplessness: validity and reliability of depressive-like states in mice. Brain Res Protoc. Dec. 2005; 16(1-3):70-8. doi: 10.1016/j.brainresprot.2005.09.002. Epub Nov. 23, 2005.
Chung et al., Segmental spinal nerve ligation model of neuropathic pain. Methods Mol Med. (2004) 99:35-45. doi: 10.1385/1-59259-770-X:035.
Cooper et al., Colocalization and coassembly of two human brain M-type potassium ctiannel subunits that are mutated in epilepsy. Proc Natl Acad Sci USA. Apr. 25, 2000;97(9):4914-9. doi: 10.1073/pnas.090092797.
Cramer et al., Development and cross-cultural translations of a 31-item quality of life in epilepsy inventory. Epilepsia. Jan. 1998;39(1):81-8. doi: 10.1111/j.1528-1157.1998.tb01278.x.
Cramer et al., Development of the Quality of Life in Epilepsy Inventory for Adolescents: the QOLIE-AD-48. Epilepsia. Aug. 1999;40(8):1114-21. doi: 10.1111/j.1528-1157.1999.tb00828.x.
Cryan et al., The tail suspension test as a model for assessing antidepressant activity: review of pharmacological and genetic studies in mice. Neurosci Biobehav Rev. 2005;29(4-5):571-625. doi: 10.1016/j.neubiorev.2005.03.009.
D'Alessio et al. Reduced expression of the glucocorticoid receptor in the hippocampus of patients with drug-resistant temporal lobe epilepsy and comorbid depression. Epilepsia. Aug. 2020;61(8):1595-1605. doi: 10.1111/epi.16598. Epub Jul. 11, 2020.
Darmani et al., Effects of the Selective α5-GABAAR Antagonist S44819 on Excitability in the Human Brain: A TMS-EMG and TMS-EEG Phase I Study. J Neurosci. Dec. 7, 2016;36(49): 12312-12320. doi: 10.1523/JNEUROSCI.1689-16.2016.
Darmani et al., Effects of antiepileptic drugs on cortical excitability in humans: A TMS-EMG and TMS-EEG study. Hum Brain Mapp. (Mar. 2019) 40(4):1276-1289. doi: 10.1002/hbm.24448.
Delmas et al., Pathways modulating neural KCNQ/M (Kv7) potassium channels. Nat Rev Neurosci. Nov. 2005;6(11):850-62. doi: 10.1038/nrn1785.
Dickenson et al., Neurobiology of neuropathic pain: mode of action of anticonvulsants. Eur J Pain. 2002:6 Suppl A:51-60. doi: 10.1053/eujp.2001.0323.
Dost et al., The anticonvulsant retigabine potently suppresses epileptiform discharges in the low Ca ++ and low Mg++ model in the hippocampal slice preparation. Epilepsy Res. Jan. 2000;38(1):53-66. doi: 10.1016/s0920-1211(99)00065-0.
Dost et al., The anti-hyperalgesic activity of retigabine is mediated by KCNQ potassium channel activation. Naunyn Schmiedebergs Arch Pharmacol. (Apr. 2004) 369(4):382-390. doi: 10.1007/s00210-004-0881-1.
Dulawa et al., Recent advances in animal models of chronic antidepressant effects: the novelty-induced hypophagia test. Neurosci Biobehav Rev. 2005;29(4-5):771-83. doi: 10.1016/j.neubiorev.2005.03.017.
Elger et al. Diagnosing and treating depression in epilepsy. Seizure. Jan. 2017:44:184-193. doi: 10.1016/j.seizure.2016.10.018. Epub Oct. 31, 2016.
Elger et al., Modern management of epilepsy: a practical approach. Epilepsy Behav. (May 2008) 12(4):501-539. doi: 10.1016/j.yebeh. 2008.01.003. Erratum in: Epilepsy Behav. (Oct. 2008) 13(3):575.
Emery, Flow Properties of Selected Pharmaceutical Powders. University of Saskatchewan Graduate Thesis. Sep. 2008. 107 pages.

Fava, M., Weight gain and antidepressants. J Clin Psychiatry. (2000) 61 Suppl 11:37-41.
Ferber et al., Concentration-effect modelling based on change from baseline to assess the prolonging effect of drugs on QTc together with an estimate of the circadian time course. J Clin Pharmacol. Dec. 2014;54(12):1400-6. doi: 10.1002/jcph.347. Epub Jun. 27, 2014.
Fisher et al., Operational classification of seizure types by the International League Against Epilepsy: Position Paper of the ILAE Commission for Classification and Terminology. Epilepsia. Apr. 2017;58(4):522-530. doi: 10.1111/epi.13670. Epub Mar. 8, 2017.
Fodor et al., Attempts to find new spasmolytics. VIII. The synthesis of 6,7-diethoxy-3-alkyl- and 6,7-diethyl-3-phenyl-isoquinolines. J Chem Soc. 1949; 1681-1682.
French et al., Effects of marketed antiepileptic drugs and placebo in the human photosensitivity screening protocol. Neurotherapeutics. Apr. 2014;11(2):412-8. doi: 10.1007/s13311-013-0243-0.
French et al., Perampanel for tonic-clonic seizures in idiopathic generalized epilepsy A randomized trial. Neurology. Sep. 15, 2015;85(11):950-7. doi: 10.1212/WNL.0000000000001930.
Friedel et al., Flupirtine: a review of its analgesic properties, and therapeutic efficacy in pain states. Drugs. Apr. 1993;45(4):548-69. doi: 10.2165/00003495-199345040-00007.
Friedman et al., Enhancing depression mechanisms in midbrain dopamine neurons achieves homeostatic resilience. Science. (Apr. 18, 2014) 344(6181):313-319. doi: 10.1126/science.1249240.
Friedman et al., Identifying depression in epilepsy in a busy clinical setting is enhanced with systematic screening. Seizure. Jul. 2009;18(6):429-33. doi: 10.1016/j.seizure.2009.03.001. Epub May 5, 2009.
Ganesan et al., Flowability and handling characteristics of bulk solids and powders—a review with implications for DDGS. Biosystems Engineering. Dec. 2008; 101(4): 425-435.
Garnett et al., Operational Characteristics of Linear concentration-QT models for assessing QTc interval in the thorough QT and Phase I clinical studies. Clin Pharmacol Ther. Aug. 2016;100(2):170-8. doi: 10.1002/cpt.361. Epub May 9, 2016.
GBD 2016 Epilepsy Collaborators, Global, regional, and national burden of epilepsy, 1990- 2016: a systematic analysis for the Global Burden of Disease Study 2016. Lancet Neurol. Apr. 2019; 18(4):357-375. doi: 10.1016/S1474-4422(18)30454-X. Epub Feb. 14, 2019.
Ghareeb et al., HPLC-ESI-MS/MS Profiling of Polyphenolics of a Leaf Extract from Alpinia zerumbet (Zingiberaceae) and Its Anti-Inflammatory, Anti-Nociceptive, and Antipyretic Activities In Vivo. Molecules. (Dec. 7, 2018) 23(12):3238. doi: 10.3390/molecules23123238.
Gilliam et al., Rapid detection of major depression in epilepsy: a multicentre study. Lancet Neurol. May 2006;5(5):399-405. doi: 10.1016/S1474-4422(06)70415-X.
Gong et al., Targeting Cre recombinase to specific neuron populations with bacterial artificial chromosome constructs. J Neurosci. (Sep. 12, 2007) 27(37):9817-9823. doi: 10.1523/JNEUROSCI.2707-07.2007.
Greenberg et al., The economic burden of adults with major depressive disorder in the United States (2005 and 2010). J Clin Psychiatry. (Feb. 2015) 76(2):155-162. doi: 10.4088/JCP. 14m09298.
Groppa et al., A practical guide to diagnostic transcranial magnetic stimulation: report of an IFCN committee. Clin Neurophysiol. Author manuscript; available in PMC Jun. 2, 2016. Published in final edited form as: Clin Neurophysiol. May 2012; 123(5): 858-882. Published online Feb. 19, 2012. doi: 10.1016/j.clinph.2012. 01.010.
Grupp et al., Protection against hypoxia-reoxygenation in the absence of poly (ADP-ribose) synthetase in isolated working hearts. J Mol Cell Cardiol. Jan. 1999;31(1):297-303. doi: 10.1006/jmcc.1998. 0864.
Gunthorpe et al., The mechanism of action of retigabine (ezogabine), a first-in-class K+ channel opener for the treatment of epilepsy. Epilepsia. Mar. 2012;53(3):412-24. doi: 10.1111/j.1528-1167.2011. 03365.x. Epub Jan. 5, 2012.

(56) References Cited

OTHER PUBLICATIONS

Guy et al., BRIEF-SR: Behavior rating inventory of executive function--self-report version: Professional manual: Psychological Assessment Resources; 2004. Overview only.
Guy et al., Test Review: Behavior Rating Inventory of Executive Function-Self- Report version. Journal of Psychoeducational Assessment. 2006;24(4):394-8.
Hamilton, Rating depressive patients. J Clin Psychiatry. Dec. 1980;41(12 Pt 2):21-4.
Hansen et al., The KCNQ channel opener retigabine inhibits the activity of mesencephalic dopaminergic systems of the rat. J Pharmacol Exp Ther. (Sep. 2006) 318(3):1006-1019. doi: 10.1124/jpet.106.106757.
He et al., Multicomplex-based pharmacophore-guided 3D-QSAR studies of N-substituted 2'-(aminoaryl)benzothiazoles as Aurora-A inhibitors. Chem Biol Drug Des. Jun. 2012;79(6):960-71. doi: 10.1111/j.1747-0285.2012.01366.x. Epub Apr. 17, 2012.
Hetka et al., Retigabine strongly reduces repetitive firing in rat entorhinal cortex. Eur J Pharmacol. (Dec. 15, 1999) 386(2-3):165-171. doi: 10.1016/s0014-2999(99)00786-4.
Hiller et al., Retigabine N-glucuronidation and its potential role in enterohepatic circulation. Drug Metab Dispos. May 1999;27(5):605-12.
Hirano et al., Kv7.2-7.5 voltage-gated potassium channel (KCNQ2-5) opener, retigabine, reduces capsaicin-induced visceral pain in mice. Neurosci Lett. (Feb. 14, 2007) 413(2):159-162. doi: 10.1016/j.neulet.2006.11.043.
Hirsch et al., ILAE definition of the Idiopathic Generalized Epilepsy Syndromes: Position statement by the ILAE Task Force on Nosology and Definitions. Epilepsia. Jun. 2022;63(6):1475-1499. doi: 10.1111/epi.17236. Epub May 3, 2022.
Hughes et al., Psychometric properties of the Generalized Anxiety Disorder 7-item scale in youth: Screening in a primary care sample. Ann Clin Psychiatry. Nov. 2021;33(4):241-250. doi: 10.12788/acp.0047.
Hunt et al., The molecular dynamics of pain control. Nat Rev Neurosci. Feb. 2001;2(2):83-91. doi: 10.1038/35053509.
Ilmoniemi et al., Methodology for combined TMS and EEG. Brain Topogr. Jan. 2010;22(4):233-48. doi: 10.1007/s10548-009-0123-4. Epub Dec. 10, 2009.
Ilmoniemi et al., Neuronal responses to magnetic stimulation reveal cortical reactivity and connectivity. Neuroreport. Nov. 10, 1997;8(16):3537-40. doi: 10.1097/00001756-199711100-00024.
Jentsch, Neuronal KCNQ potassium channels; physiology and role in disease. Nat Rev Neurosci. Oct. 2000;1(1):21-30. doi: 10.1038/35036198.
Jiang et al., X-ray structure of a voltage-dependent K+ channel. Nature. May 1, 2003;423(6935):33-41. doi: 10.1038/nature01580.
Johnson et al., Psychometric Properties of the General Anxiety Disorder 7-Item (GAD-7) Scale in a Heterogeneous Psychiatric Sample. Front Psychol. Aug. 6, 2019:10:1713. doi: 10.3389/fpsyg.2019.01713. eCollection 2019.
Johnston et al., The burden of treatment-resistant depression: A systematic review of the economic and quality of life literature. J Affect Disord. (Jan. 1, 2019) 242:195-210. doi: 10.1016/j.jad.2018.06.045.
Kahkonen et al., Transcranial magnetic stimulation: applications for neuropsychopharmacology. J Psychopharmacol. Jun. 2004; 18(2):257-61. doi: 10.1177/0269881104042631.
Kanner et al. Depression and epilepsy: epidemiologic and neurobiologic perspectives that may explain their high comorbid occurrence. Epilepsy Behav. Jun. 2012;24(2):156-68. doi: 10.1016/j.yebeh.2012.01.007.
Kasteleijn-Nolst Trenité et al., Kv7 potassium channel activation with ICA-105665 reduces photoparoxysmal EEG responses in patients with epilepsy. Epilepsia. Aug. 2013;54(8):1437-43. doi: 10.1111/epi.12224. Epub May 20, 2013.
Keel et al., A safety screening questionnaire for transcranial magnetic stimulation. Clin Neurophys. Apr. 2001;112(4):720. doi: 10.1016/s1388-2457(00)00518-6.

Kharkovets et al., Mice with altered KCNQ4 KT channels implicate sensory outer hair cells in human progressive deafness. EMBO J. Feb. 8, 2006;25(3):642-52. doi: 10.1038/sj.emboj.7600951. Epub Jan. 26, 2006.
Kibbe, Handbook of Pharmaceutical Excipients (Pharmaceutical Press, London) (2000).
Krishnan et al., Molecular adaptations underlying susceptibility and resistance to social defeat in brain reward regions. Cell. (Oct. 19, 2007) 131(2):391-404. doi: 10.1016/j.cell.2007.09.018.
Kubisch et al., KCNQ4, a novel potassium channel expressed in sensory outer hair cells, is mutated in dominant deafness. Cell. Feb. 5, 1999;96(3):437-46. doi: 10.1016/s0092-8674(00)80556-5.
Kuo et al., Inhibition of Na(+) current by diphenhydramine and other diphenyl compounds: molecular determinants of selective binding to the inactivated channels. Mol Pharmacol. Jan. 2000;57(1):135-43.
Kuzma et al., Progress in the development of ultra-long-acting local anesthetics. Reg Anesth. Nov.-Dec. 1997;22(6):543-51.
Kwan et al., Early identification of refractory epilepsy. N Engl J Med. Feb. 3, 2000;342(5):314-9. doi: 10.1056/NEJM200002033420503.
Lamas et al., Effects of a cognition-enhancer, linopirdine (DuP 996), on M-type potassium currents (IK(M)) and some other voltage- and ligand-gated membrane currents in rat sympathetic neurons. Eur J Neurosci. Mar. 1997;9(3):605-16. doi: 10.1111/j.1460-9568.1997.tb01637.x.
Lange et al., Refinement of the binding site and mode of action of the anticonvulsant Retigabine on KCNQ K+ channels. Mol Pharmacol. Feb. 2009;75(2):272-80. doi: 10.1124/mol.108.052282. Epub Nov. 17, 2008.
Lee et al., Structure of the KvAP voltage-dependent K+ channel and its dependence on the lipid membrane. Proc Natl Acad Sci USA. Oct. 25, 2005;102(43):15441-6. doi: 10.1073/pnas.0507651102. Epub Oct. 13, 2005.
Legoix et al., Characterizing powders in order to determine their flow behavior in a mixer: From small scale observations to macroscopic in-mixer rheology for powders of various flowabilities. Powder Technology. 2017; 322: 314-331. 10.1016/j.powtec.2017.07.075. hal-01617227.
Levenson et al., Statistical Review and Evaluation—Antiepileptic Drugs and Suicidality. United States Food and Drug Administration. May 2008. 45 pages.
Long et al., Crystal structure of a mammalian voltage-dependent Shaker family K+ channel. Science. Aug. 5, 2005;309(5736):897-903. doi: 10.1126/science.1116269. Epub Jul. 7, 2005.
Lukyanetz et al., Selective blockade of N-type calcium channels by levetiracetam. Epilepsia. (Jan. 2002) 43(1):9-18. doi: 10.1046/j.1528-1157.2002.24501.x.
Main et al., Modulation of KCNQ2/3 potassium channels by the novel anticonvulsant retigabine. Mol Pharmacol. Aug. 2000;58(2):253-62. doi: 10.1124/mol.58.2.253.
Maki et al., The relationship between peripheral and early cortical activation induced by transcranial magnetic stimulation. Neurosci Lett. Jun. 30, 2010;478(1):24-8. doi: 10.1016/j.neulet.2010.04.059. Epub Apr. 29, 2010.
Mandal, Chapter 2 Preformulation and Product Development in: Manufacturing of Halal Pharmaceuticals. First Edition. Jan. 2015; pp. 2-1 to 2-21. IIUM Press, eds.
Marrion, Control of M-current. Annu Rev Physiol. 1997:59:483-504. doi: 10.1146/annurev.physiol.59.1.483.
Massimini et al., Breakdown of cortical effective connectivity during sleep. Science. Sep. 30, 2005;309(5744):2228-32. doi: 10.1126/science.1117256.
Matysina et al., Surface Structure, Roughness, Energy and Texture Of Crystals. J Phys Chem Solids. 1992; 53(1): 167-174.
Meshkat et al., The role of KCNQ channel activators in management of major depressive disorder. J Affect Disord. Aug. 15, 2024:359:364-372. doi: 10.1016/j.jad.2024.05.067. Epub May 19, 2024.
Nair et al., A simple practice guide for dose conversion between animals and human. J Basic Clin Pharm. (Mar. 2016) 7(2):27-31. doi: 10.4103/0976-0105.177703.
Nakonezny et al., Evaluation of anhedonia with the Snaith-Hamilton Pleasure Scale (SHAPS) in adult outpatients with major

(56) References Cited

OTHER PUBLICATIONS depressive disorder. J Psychiatr Res. (Jun. 2015) 65:124-130. doi: 10.1016/j.jpsychires.2015.03.010. Author Manuscript, 16 pages.
Namdari et al., Pharmacokinetics of XEN496, a Novel Pediatric Formulation of Ezogabine, Under Fed and Fasted Conditions: A Phase 1 Trial. Neurol Ther. Jun. 2022; 11(2):781-796. doi: 10.1007/s40120-022-00343-x. Epub Apr. 5, 2022.
Nestler et al., The mesolimbic dopamine reward circuit in depression. Biol Psychiatry. (Jun. 15, 2006) 59(12):1151-1159. doi: 10.1016/j.biopsych.2005.09.018.
Nicholas et al., Trends in antiepileptic drug utilisation in UK primary care 1993-2008: cohort study using the General Practice Research Database. Seizure. Jul. 2012;21(6):466-70. doi: 10.1016/j.seizure.2012.04.014. Epub May 19, 2012.
Nielsen et al., Intracranial self-stimulation and sucrose intake differ as hedonic measures following chronic mild stress: interstrain and interindividual differences. Behav Brain Res. Jan. 2000;107(1-2):21-33. doi: 10.1016/s0166-4328(99)00110-2.
Nikouline et al., The role of the coil click in TMS assessed with simultaneous EEG. Clin Neurophysiol. Aug. 1999;110(8):1325-8. doi: 10.1016/s1388-2457(99)00070-x.
Otto et al., Effects of the Anticonvulsant Retigabine on Cultured Cortical Neurons: Changes in Electroresponsive Properties and Synaptic Transmission. Mol Pharmacol. Apr. 2002;61(4):921-7. doi: 10.1124/mol.61.4.921.
Parcej et al., Structural characterisation of neuronal voltage-sensitive K+ channels heterologously expressed in Pichia pastoris. J Mol Biol. Oct. 10, 2003;333(1): 103-16. doi: 10.1016/j.jmb.2003.07.009.
Passmore et al., KCNQ/M currents in sensory neurons: significance for pain therapy. J Neurosci. Aug. 6, 2003;23(18):7227-36. doi: 10.1523/JNEUROSCI.23-18-07227.2003.
Patani et al., Bioisosterism: A Rational Approach in Drug Design. Chem Rev. Dec. 19, 1996;96(8):3147-3176. doi: 10.1021/cr950066q.
Pavao-de-Souza et al., Acetic acid- and phenyl-p-benzoquinone-induced overt pain-like behavior depends on spinal activation of MAP kinases, PI(3)K and microglia in mice. Pharmacol Biochem Behav. (May 2012) 101(3):320-328. doi: 10.1016/j.pbb.2012.01.018.
Phend, Novel Agent Promising as Add-On Epilepsy Treatment -Phase IIb trial shows benefit for the most common type of epileptic seizures. MedPage Today. Oct. 9, 2023; 4 pages. Retrieved from the Internet: URL:https://www.medpagetoday.com/neurology/seizures/106688.
Podczeck et al., The influence of particle size and shape on the angle of internal friction and the flow factor of unlubricated and lubricated powders. International Journal of Pharmaceutics. Nov. 29, 1996; 144(2): 187-194.
Porter et al., Retigabine. Neurotherapeutics. Jan. 2007;4(1):149-54. doi: 10.1016/j.nurt.2006.11.012.
Posner et al., The Columbia-Suicide Severity Rating Scale: initial validity and internal consistency findings from three multisite studies with adolescents and adults. Am J Psychiatry. Dec. 2011;168(12):1266-77. doi: 10.1176/appi.ajp.2011.10111704.
Premoli et al., The impact of GABAergic drugs on TMS-induced brain oscillations in human motor cortex. Neuroimage. Dec. 2017: 163:1-12. doi: 10.1016/j.neuroimage.2017.09.023. Epub Sep. 14, 2017.
Premoli et al., TMS-EEG signatures of GABAergic neurotransmission in the human cortex. J Neurosci. Apr. 16, 2014;34(16):5603-12. doi: 10.1523/JNEUROSCI.5089-13.2014.
Prescott et al., Pigmentary abnormalities (discoloration) associated with ezogabine/retigabine treatment: nonclinical aspects (Poster 2.324). Presented at the 68th Annual Meeting of the American Epilepsy Society (AES), Seattle, Washington, U.S.A., Dec. 6, 2014. Accessed at: https://aesnet.org/abstractslisting/pigmentary-abnormalities-(discoloration)-associated-with-ezogabine/retigabine-treatment--nonclinical-aspects.

Reich et al., Design and synthesis of novel 6,7-imidazotetrahydroquinoline inhibitors of.thymidylate synthase using iterative protein crystal structure analysis. J Med Chem. Mar. 6, 1992;35(5):847-58. doi: 10.1021/jm00083a007.
Reis et al., Contribution of transcranial magnetic stimulation to the understanding of cortical mechanisms involved in motor control. J Physiol. Jan. 15, 2008;586(2):325-51. doi: 10.1113/jphysiol.2007.144824. Epub Nov. 1, 2007.
Rizvi et al., Assessing anhedonia in depression: Potentials and pitfalls. Neurosci Biobehav Rev. (Jun. 2016) 65:21-35. doi: 10.1016/j.neubiorev.2016.03.004.
Rogasch et al., Assessing cortical network properties using TMS-EEG. Hum Brain Mapp. Jul. 2013;34(7):1652-69. doi: 10.1002/hbm.22016. Epub Feb. 29, 2012.
Rogawski et al., New molecular targets for antiepileptic drugs: alpha(2)delta, SV2A, and K(v)7/KCNQ/M potassium channels. Curr Neurol Neurosci Rep. Jul. 2008;8(4):345-52. doi: 10.1007/s11910-008-0053-7.
Rogawski et al., The neurobiology of antiepileptic drugs. Nat Rev Neurosci. Jul. 2004;5(7):553-64. doi: 10.1038/nrn1430.
Rogawski, KCNQ2/KCNQ3 K+ channels and the molecular pathogenesis of epilepsy: implications for therapy. Trends Neurosci. Sep. 2000;23(9):393-8. doi: 10.1016/s0166-2236(00)01629-5.
Rossi et al., The Safety of TMS Consensus Group. Safety, ethical considerations, and application guidelines for the use of transcranial magnetic stimulation in clinical practice and research. Clin Neurophysiol. Author manuscript; available in PMC Jan. 18, 2012. Published in final edited form as: Clin Neurophysiol. Dec. 2009; 120(12): 2008-2039. Published online Oct. 14, 2009. doi: 10.1016/j.clinph.2009.08.016.
Rostock et al., D-23129: a new anticonvulsant with a broad spectrum activity in animal models of epileptic seizures. Epilepsy Res. Apr. 1996;23(3):211-23. doi: 10.1016/0920-1211(95)00101-8.
Rundfeldt et al., Multiple actions of the new anticonvulsant D-23129 on voltage-gated inward currents and GABA-induced currents in cultured neuronal cells (abstract). Naunyn-Schmiedeberg's Arch Pharmacol. 1995; 351 (Suppl):R160.
Rundfeldt, Characterization of the K+ channel opening effect of the anticonvulsant retigabine in PC12 cells. Epilepsy Res. Jun. 1999;35(2):99-107. doi: 10.1016/s0920-1211(98)00131-4.
Rundfeldt, The new anticonvulsant retigabine (D-23129) acts as an opener of K+ channels in neuronal cells. Eur J Pharmacol. Oct. 8, 1997;336(2-3):243-9. doi: 10.1016/s0014-2999(97)01249-1.
Rush et al., Acute and longer-term outcomes in depressed outpatients requiring one or several treatment steps: a STAR*D report. Am J Psychiatry. (Nov. 2006) 163(11):1905-1917. doi: 10.1176/ajp.2006.163.11.1905.
Rush et al., Sequenced treatment alternatives to relieve depression (STAR*D): rationale and design. Control Clin Trials. (Feb. 2004) 25(1):119-142. doi: 10.1016/s0197-2456(03)00112-0.
Sanguinetti et al., Coassembly of K(V)LQT1 and minK (IsK) proteins to form cardiac I(Ks) potassium channel. Nature. Nov. 7, 1996;384(6604):80-3. doi: 10.1038/384080a0.
Schroeder et al., KCNQ5, a novel potassium channel broadly expressed in brain, mediates M-type currents J Biol Chem. Aug. 4, 2000;275(31):24089-95. doi: 10.1074/jbc.M003245200.
Schroeder et al., Moderate loss of function of cyclic-AMP-modulated KCNQ2/KCNQ3 K+ channels causes epilepsy. Nature. Dec. 17, 1998;396(6712):687-90. doi: 10.1038/25367.
Scott et al., Anxiety and depressive disorders in people with epilepsy: A meta-analysis. Epilepsia. Jun. 2017;58(6):973-982. doi: 10.1111/epi.13769. Epub May 3, 2017.
Shah et al., Influence of particle properties on powder bulk behaviour and processability. Int J Pharm. Feb. 25, 2017;518(1-2):138-154. doi: 10.1016/j.ijpharm.2016.12.045. Epub Dec. 23, 2016.
Shieh et al., Potassium channels: molecular defects, diseases, and therapeutic opportunities. Pharmacol Rev. Dec. 2000;52(4):557-94.
Singh et al., A novel potassium channel gene, KCNQ2, is mutated in an inherited epilepsy of newborns. Nat Genet. Jan. 1998; 18(1):25-9. doi: 10.1038/ng0198-25.
Snaith et al., A scale for the assessment of hedonic tone the Snaith-Hamilton Pleasure Scale. Br J Psychiatry. (Jul. 1995) 167(1):99-103. doi: 10.1192/bjp.167.1.99.

(56) References Cited

OTHER PUBLICATIONS

Sotty et al., Antipsychotic-like effect of retigabine [N-(2-Amino-4-(fluorobenzylamino)-phenyl)carbamic acid ester], a KCNQ potassium channel opener, via modulation of mesolimbic dopaminergic neurotransmission. J Pharmacol Exp Ther. (Mar. 2009) 328(3):951-962. doi: 10.1124/jpet.108.146944.
Spitzer et al., A brief measure for assessing generalized anxiety disorder: the GAD-7. Arch Intern Med. May 22, 2006;166(10):1092-7. doi: 10.1001/archinte.166.10.1092.
Stewart et al., Development and testing of the Migraine Disability Assessment (MIDAS) Questionnaire to assess headache-related disability. Neurology. 2001;56(6 Suppl 1):S20-8. doi: 10.1212/wnl.56.suppl_1.s20.
Suzuki et al., Neuropathic pain: nerves bursting with excitement. NeuroReport. Aug. 21, 2000;11(12):R17-21. doi: 10.1097/00001756-200008210-00001.
Taniguchi et al., A resource of Cre driver lines for genetic targeting of GABAergic neurons in cerebral cortex. Neuron. (Sep. 22, 2011) 71(6):995-1013. doi: 10.1016/j.neuron.2011.07.026.
Tatulian et al., Activation of expressed KCNQ potassium currents and native neuronal M-type potassium currents by the anti-convulsant drug retigabine. J Neurosci. Aug. 1, 2001;21(15):5535-45. doi: 10.1523/JNEUROSCI.21-15-05535.2001.
Tatulian et al., Effect of the KCNQ potassium channel opener retigabine on single KCNQ2/3 channels expressed in CHO cells. J Physiol. May 15, 2003;549(Pt 1):57-63. doi: 10.1113/jphysiol.2003.039842. Epub Apr. 17, 2003.
Tober et al., D-23129: a potent anticonvulsant in the amygdala kindling model of complex partial seizures. Eur J Pharmacol. May 15, 1996;303(3):163-9. doi: 10.1016/0014-2999(96)00073-8.
Touboul et al., A Comparative evaluation of the effects of Propafenone and lidocaine on early ventricular arrhythmias after acute myocardial infarction. Eur Heart J. Nov. 1988;9(11):1188-93. doi: 10.1093/oxfordjournals.eurheartj.a062428.
Tung, Industrial Perspectives of Pharmaceutical Crystallization. Org Process Res Dev. 2013; 17(3): 445-454. https://doi.org/10.1021/op3002323.
Tye et al., Dopamine neurons modulate neural encoding and expression of depression-related behaviour. Nature. (Jan. 24, 2013) 493(7433):537-541. doi: 10.1038/nature11740. Author Manuscript, 19 pages.
Verrotti et al., Photosensitivity: epidemiology, genetics, clinical manifestations, assessment, and management. Epileptic Disord. Dec. 2012; 14(4):349-62. doi: 10.1684/epd.2012.0539.
Vippagunta et al., Crystalline solids. Adv Drug Deliv Rev. May 16, 2001;48(1):3-26. doi: 10.1016/s0169-409x(01)00097-7.
Virtanen et al., Instrumentation for the measurement of electric brain responses to transcranial magnetic stimulation. Med Biol Eng Comput. May 1999;37(3):322-6. doi: 10.1007/BF02513307.
Von Bebenburg et al., Substituierte Polyaminopyridine. Chemiker-Zeitung. 1979; 103:387-399. (German language article attached.).
Vrieze et al., Reduced reward learning predicts outcome in major depressive disorder. Biol Psychiatry. (Apr. 1, 2013) 73(7):639-645. doi: 10.1016/j.biopsych.2012.10.014. Author Manuscript, 17 pages.
Wang et al., KCNQ2 and KCNQ3 potassium channel subunits: molecular correlates of the M-channel. Science. Dec. 4, 1998;282(5395):1890-3. doi: 10.1126/science.282.5395.1890.
Wang et al., Positional cloning of a novel potassium channel gene: KVLQT1 mutations cause cardiac arrhythmias. Nat Genet. Jan. 1996;12(1):17-23. doi: 10.1038/ng0196-17.
Watanbe et al., Disruption of the epilepsy KCNQ2 gene results in neural hyperexcitability. J Neurochem. Jul. 2000;75(1):28-33. doi: 10.1046/j.1471-4159.2000.0750028.x.
Werhahn et al. A randomized, double-blind comparison of antiepileptic drug treatment in the elderly with new-onset focal epilepsy. Epilepsia. (Mar. 2015) 56(3):450-459. doi: 10.1111/epi.12926.
West, Solid State Chemistry and Its Applications. John Wiley & Sons, New York, eds. 1988. pp. 358 and 365.
Wickenden et al., KCNQ potassium channels: drug targets for the treatment of epilepsy and pain. Exp Opin Thera Patents. 2004; 14(4): 457-469.
Wickenden et al., Retigabine, a novel anti-convulsant, enhances activation of KCNQ2/Q3 potassium channels. Mol Pharmacol. Sep. 2000;58(3):591-600. doi: 10.1124/mol.58.3.591.
Wolf (ed.), Burger's Medicinal Chemistry and Drug Discovery, 5th Edition vol. 1: Principles and Practice, John Wiley & Sons, New York, DD. 975-977 (1995).
Wood et al., Voltage-gated sodium channels and pain pathways. J Neurobiol. Oct. 2004;61(1):55-71. doi: 10.1002/neu.20094.
Wu et al., Discovery of (S,E)-3-(2-fluorophenyl)-N-(1-(3-(pyridin-3-yloxy)phenyl)ethyl)-acrylamide as a potent and efficacious KCNQ2 (Kv7.2) opener for the treatment of neuropathic pain. Bioorg Med Chem Lett. (Nov. 15, 2013) 23(22):6188-6191. doi: 10.1016/j.bmcl.2013.08.092.
Wu et al., Regulatory perspectives of Type II prod rug development and time-dependent toxicity management: nonclinical Pharm/Tox analysis and the role of comparative toxicology. Toxicology. Jul. 1, 2007;236(1-2):1-6. doi: 10.1016/j.tox.2007.04.005. Epub Apr. 21, 2007.
Wuttke, The new anticonvulsant retigabine favors voltage-dependent opening of the Kv7.2 (KCNQ2) channel by binding to its activation gate. Mol Pharmacol. Apr. 2005;67(4):1009-17. doi: 10.1124/mol.104.010793. Epub Jan. 20, 2005.
Yu et al., Prediction of Bulk Powder Flow Performance Using Comprehensive Particle Size and Particle Shape Distributions. J Pharm Sci. Jan. 2011;100(1):284-93. doi: 10.1002/jps.22254. Epub Jun. 22, 2010.
Yu et al., What is the "typical" particle shape of active pharmaceutical ingredients? Powder Technology. May 15, 2017; 313: 1-8. https://doi.org/10.1016/j.powtec.2017.02.043.
Zani et al., Sodium channels are required during in vivo sodium chloride hyperosmolarity to stimulate increase in intestinal endothelial nitric oxide production. Am J Physiol Heart Circ Physiol. Jan. 2005;288(1):H89-95. doi: 10.1152/ajpheart.00644.2004. Epub Aug. 26, 2004.
Ziemann et al., Effects of antiepileptic drugs on motor cortex excitability in humans: a transcranial magnetic stimulation study. Ann Neurol. Sep. 1996;40(3):367-78. doi: 10.1002/ana.410400306.
Ziemann et al., TMS and drugs revisited 2014. Clin Neurophysiol. (Oct. 2015) 126(10):1847-1868. doi: 10.1016/j.clinph.2014.08.028.
Ziemann, TMS and drugs. Clin Neurophysiol. Aug. 2004;115(8):1717-29. doi: 10.1016/j.clinph.2004.03.006.

METHODS OF TREATING DEPRESSIVE DISORDERS

RELATED APPLICATIONS

This application claims priority under 35 U.S.C. § 119 (e) to U.S. provisional patent application, U.S. Ser. No. 62/932,724, filed on Nov. 8, 2019, the entire contents of which is incorporated herein by reference.

1. BACKGROUND

Depressive disorders affect more than 20 million adults in United States. Depressive disorders are characterized by sadness severe enough or persistent enough to interfere with function and often by decreased interest or pleasure in activities. The *Diagnostic and Statistical Manual of Mental Disorders*, Fifth Edition (DSM-5) classifies some depressive disorders by specific symptoms, such as major depressive disorder (often called major depression) or persistent depressive disorder (dysthymia), and others by etiology, such as premenstrual dysphoric disorder, depressive disorder due to another medical condition, or substance/medication-induced depressive disorder. Another type of depressive disorder includes bipolar disorder (manic-depressive illness). The exact cause(s) of depressive disorders are unknown, but genetic and environmental factors are known to contribute.

First-line treatments of depressive disorders typically include one or more of support, psychotherapy, and antidepressant drugs. Several drug classes and drugs can be used to treat depressive disorders, such selective serotonin reuptake inhibitors (SSRIs), serotonin modulators (5-HT$_2$ blockers), serotonin-norepinephrine reuptake inhibitors (SNRIs), norepinephrine-dopamine reuptake inhibitors, atypical antidepressants, tricyclic antidepressants, monoamine oxidase inhibitors (MAOIs), melatonergic antidepressants, and ketamine-like drugs, with SSRIs often being the initial drug of choice. However for many, finding the right antidepressant treatment for depressive disorders can take a trial-and-error approach, as some antidepressants are only partially effective and are associated with additional limitations, including a slow onset of therapeutic action and undesirable side effects. Most approved antidepressants share the same serotonergic and noradrenergic pathways that limit mechanistic diversity and leave little opportunity for improved patient outcomes or personalized treatment approaches.

Due to the number of adults affected, the number and complexity of disorder classes, and the often ineffectiveness and mechanistic homogeneity of first-line antidepressants, there remains a need in the art for novel and effective treatments of depressive disorders, including major depression. The present disclosure addresses this need by providing compositions and methods and uses for treating depressive disorders, and offers other related advantages.

2. SUMMARY

The present disclosure describes certain methods and uses for the small molecule N-[4-(6-Fluoro-3,4-dihydro-1H-isoquinolin-2-yl)-2,6-dimethylphenyl]-3,3-dimethylbutanamide (herein referred to as "Compound A").

In one embodiment, the present disclosure is directed to a method of treating a depressive disorder in a human in need thereof, comprising administering a therapeutically effective amount of Compound A to the human. In certain instances, the depressive disorder treated by the administration of Compound A is major depressive disorder (MDD), disruptive mood dysregulation disorder, persistent depressive disorder, bipolar spectrum disorder, postpartum depression, premenstrual dysphoric disorder (PMDD), seasonal affective disorder (SAD), atypical depression, treatment-resistant depression (TRD), depression associated with agitation or anxiety, adjustment disorder with depressed mood, prolonged depressive reaction, or a combination thereof. In certain embodiments, the depressive disorder treated by the administration of Compound A is major depressive disorder (MDD).

In an additional embodiment, the method of treating a depressive disorder comprising administering a therapeutically effective amount of Compound A further comprises enhancing the opening of a Kv7 potassium channel in the human.

In another embodiment, the present disclosure is directed to a method of opening or enhancing the opening of a Kv7 potassium channel in a human, comprising administering an effective amount of Compound A to the human, wherein the human has a depressive disorder, such as those described herein.

In some aspects, the Kv7 potassium channel is one or more of Kv7.2, Kv7.3, Kv7.4, or Kv7.5. In certain instances, the opening or enhanced opening of one or more of the Kv7.2, Kv7.3, Kv7.4, or Kv7.5 potassium channels is selective over Kv7.1. In other instances, the method comprises opening or enhanced opening of the Kv7.2/Kv7.3 (KCNQ2/3) potassium channel.

In one embodiment, the present disclosure provides a method of treating a depressive disorder in a human in need thereof, wherein Compound A is orally administered to the human. In certain instances, the oral administration to the human comprises a dose of 2 to 200 mg of Compound A per administration. In other instances, the oral administration to the human comprises a dose of 5-1000 mg per day.

Compound A is a small molecule currently being developed for the treatment of seizure disorders, and its use as a potassium channel modulator is disclosed in U.S. Pat. Nos. 8,293,911 and 8,993,593 as well as U.S. application Ser. Nos. 16/409,684 and 16/410,851, the disclosures of which are hereby incorporated by reference in their entireties.

These and other aspects of this disclosure will be apparent upon reference to the following detailed description. To this end, various references are set forth herein which describe in more detail certain background information and procedures and are each hereby incorporated by reference in their entirety.

3. BRIEF DESCRIPTION OF THE DRAWINGS

Figure 4:
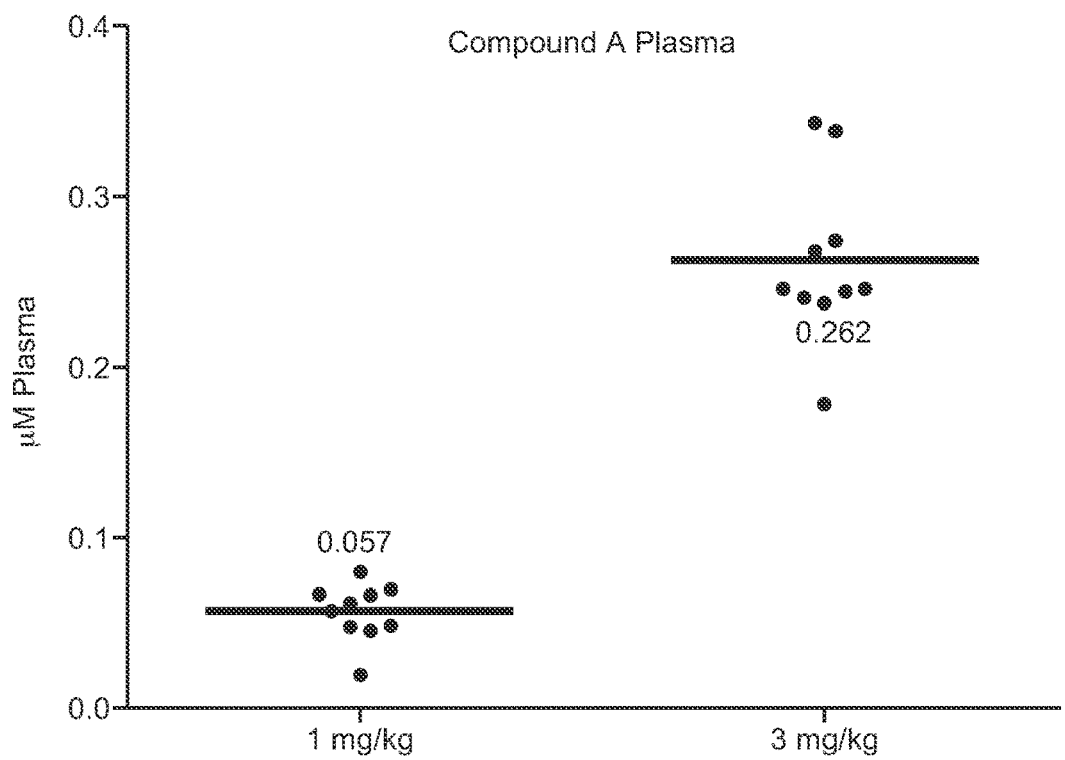
Figure 4:
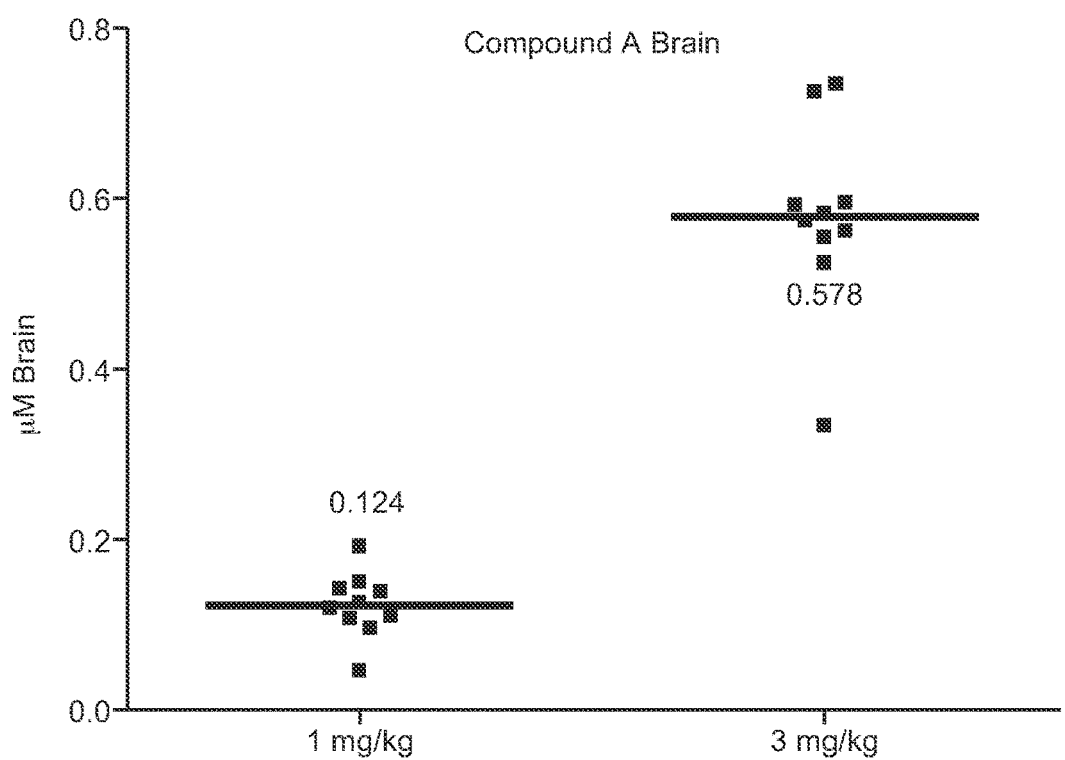

FIG. 4 includes graphical representations of Compound A concentration in plasma and brain (μM, y-axes) for 1 mg/kg and 3 mg/kg dosing (x-axes).

4. DETAILED DESCRIPTION

The present disclosure relates to novel and improved methods and uses for Compound A, particularly for treatment of depressive disorders by administering Compound A to a human patient in need thereof, including by oral administration.

In the following disclosure, certain specific details are set forth in order to provide a thorough understanding of various embodiments. However, one skilled in the art will understand that the methods and uses described herein may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

4.1. Definitions

As used in the specification and appended claims, unless specified to the contrary, the following terms and abbreviations have the meaning indicated:

"Compound A" refers to the compound having the following formula:

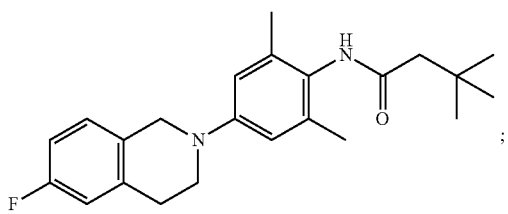 [SMILES: Cc1cc(N2CCc3cc(F)ccc3C2)cc(C)c1NC(=O)CC(C)(C)C]

and having a chemical name of N-[4-(6-fluoro-3,4-dihydro-1H-isoquinolin-2-yl)-2,6-dimethylphenyl]-3,3-dimethylbutanamide. Preparation of Compound A and its use as a Kv7.2/Kv7.3 (KCNQ2/3) opener is disclosed in U.S. Pat. Nos. 8,293,911 and 8,993,593 as well as U.S. application Ser. Nos. 16/409,684 and 16/410,851. Compound A is different from most known AED's in that it potentiates and enhances opening of the voltage-gated potassium channels Kv7.2 and Kv7.3 (Kv7.2/Kv7.3), which are important in controlling neuronal excitability. Compound A is used in the methods and uses described herein.

"Therapeutically effective amount" as used herein refers to an amount of Compound A that is sufficient to treat the stated disease, disorder, or condition or have the desired stated effect on the disease, disorder, or condition or one or more mechanisms underlying the disease, disorder, or condition in a human subject. In certain embodiments, when Compound A is administered for the treatment of a depressive disorder, therapeutically effective amount refers an amount of Compound A which, upon administration to a human, treats or ameliorates a depressive disorder in the human, or exhibits a detectable therapeutic effect in the human having a depressive disorder. The effect can be detected by, for example, a reduction in the number of depressive episodes or by the reduction of the severity of depressive episodes.

"Treatment" as used herein refers to therapeutic applications associated with administering Compound A that ameliorate the indicated disease, disorder, or condition or one or more underlying mechanisms of said disease, disorder, or condition, including slowing or stopping progression of the disease, disorder or condition or one or more of the underlying mechanisms in a human subject. In certain embodiments, when Compound A is administered for the treatment of a depressive disorder, treatment refers to therapeutic applications to slow or stop progression of a depressive disorder and/or reversal of a depressive disorder. Reversal of a depressive disorder differs from a therapeutic application which slows or stops a depressive disorder in that with a method of reversing, not only is progression of a depressive disorder stopped, cellular behavior is moved to some degree toward a normal state that would be observed in the absence of the depressive disorder. In some embodiments, the treatment of a depressive disorder comprising the administration of Compound A is accompanied by an alteration of the cellular activity of one or more Kv7 potassium channels (e.g., Kv7.2, Kv7.3, Kv7.4, and/or Kv7.5, particularly Kv7.2 and/or Kv7.3, optionally over Kv7.1) toward a normal level that would be observed in the absence of the depressive disorder.

"Under fed conditions" refers to the condition of having consumed food during the time period between from about 4 hours prior to the oral administration of an effective amount (e.g., within the therapeutically effective dose range) of Compound A to about 4 hours after the administration of Compound A. The food may be a solid, liquid, or mixture of solid and liquid food with sufficient bulk and fat content that it is not rapidly dissolved and absorbed in the stomach. In some instances, the food is a meal, such as breakfast, lunch, dinner or, alternatively, baby food (e.g., formula or breast milk). The therapeutically effective amount of Compound A may be orally administered to the subject, for example, between about 30 minutes prior to about 2 hours after eating a meal, most advantageously, the dosage unit of Compound A is orally administered during a meal or within 15 minutes after eating a meal.

"Under fasted conditions" refers to the condition of not having consumed food during the time period between from at least 4 hours prior to the oral administration of a therapeutically effective amount of Compound A to about 4 hours after administration of Compound A.

4.2. Embodiments

In some embodiments, the present disclosure is directed to a method of treating a depressive disorder in a human in need thereof, comprising administering (e.g., orally) a therapeutically effective amount of Compound A to the human. In certain instances, the depressive disorder treated comprising the administration of Compound A is major depressive disorder (MDD), disruptive mood dysregulation disorder, persistent depressive disorder, bipolar spectrum disorder, postpartum depression, premenstrual dysphoric disorder (PMDD), seasonal affective disorder (SAD), atypical depression, treatment-resistant depression (TRD), depression associated with agitation or anxiety, or a combination thereof. In certain embodiments, the amount of Compound A administered is sufficient to reduce the severity of the depressive disorder, the frequency of the depressive disorder, or both. In certain embodiments, the depressive disorder treated comprising the administration of Compound A is major depressive disorder (MDD).

In some embodiments, the method of treating a depressive disorder by administering a therapeutically effective amount of Compound A comprises enhancing the opening of a Kv7 potassium channel in the human.

In further embodiments, the present disclosure is directed to a method of treating obsessive-compulsive disorder (OCD), panic disorder, social anxiety disorder, social phobia, agoraphobia, agoraphobia with panic disorder, hypochondriasis, post-traumatic stress disorder (PTSD), treatment-resistant bipolar disorder, generalized anxiety disorder, attention-deficit/hyperactivity disorder (ADHD), bipolar I disorder, bipolar II disorder, manic disorder, cyclothymic disorder and bipolar disorder not otherwise specified, dysthymic disorder, depressive disorder not otherwise specified, minor depression, recurrent brief depressive disorder, depressive-type psychosis, impulse-control disorders, schizophrenia, schizophreniform disorder, schizoaffective disorder, Parkinson's disease, dementia, Alzheimer's disease, Huntington's disease, Tourette's syndrome, aggression, and substance use and/or abuse, or a combination thereof, comprising administering a therapeutically effective amount of Compound A to a human in need thereof.

In certain embodiments, the present disclosure provides a method or use comprising opening or enhancing the opening of a Kv7 potassium channel, such as the Kv7.2, Kv7.3, Kv7.4, and/or Kv7.5 potassium channel, particularly the Kv7.2/Kv7.3 (KCNQ2/3) potassium channel in a human in need thereof by administering an effective amount of Compound A. In some such embodiments, the human has a depressive disorder, such as those described herein.

In certain instances, the method or use described herein comprises selectively opening or enhancing the opening of a Kv7 potassium channel, such as one or more of Kv7.2, Kv7.3, Kv7.4, or Kv7.5 over Kv7.1. In some embodiments, the method or use is selective for Kv7.2, over Kv7.1. In other embodiments, the method or use is selective for Kv7.3, over Kv7.1. In yet other embodiments, the method or use is selective for Kv7.4, over Kv7.1. In yet further other embodiments, the method or use is selective for Kv7.5, over Kv7.1. In certain embodiments, the method or use is selective for Kv7.2 and Kv7.3, over Kv7.1. In certain embodiments, the method or use is selective for Kv7.2 and Kv7.3 over other Kv7 potassium channels. In certain embodiments, the method or use is selective for Kv7.2 and Kv7.3 over Kv7.4 and Kv7.5.

In one embodiment, the methods and uses described herein, such as the method of or use in treating a depressive disorder in a human in need thereof, is achieved by administering (e.g., orally) a therapeutically effective amount of Compound A, such as from about 0.05 mg/kg to about 2.0 mg/kg. More specific representative amounts include 0.05 mg/kg, 0.10 mg/kg, 0.20 mg/kg, 0.30 mg/kg, 0.40 mg/kg, 0.5 mg/kg, 0.6 mg/kg, 0.7 mg/kg, 0.80 mg/kg, 0.90 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg and 2.0 mg/kg, or any range of amounts created by using two of the aforementioned amounts as endpoints. In some aspects, the method or use includes administering (e.g., orally) 0.1-1.0 mg/kg of Compound A. In some aspects, the method includes administering (e.g., orally) 0.2-0.5 mg/kg of Compound A.

In some embodiments, the methods and uses described herein, such as the method of or use in treating a depressive disorder in a human in need thereof, is achieved by administering (e.g., orally) a therapeutically effective amount of Compound A, such as 2 to 200 mg of Compound A in a single or divided doses. For example, the method can include administering (e.g., orally), in a single or divided doses, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 101 mg, about 102 mg, about 103 mg, about 104 mg, about 105 mg, about 106 mg, about 107 mg, about 108 mg, about 109 mg, about 110 mg, about 111 mg, about 112 mg, about 113 mg, about 114 mg, about 115 mg, about 116 mg, about 117 mg, about 118 mg, about 119 mg, about 120 mg, about 121 mg, about 122 mg, about 123 mg, about 124 mg, about 125 mg, about 126 mg, about 127 mg, about 129 mg, about 130 mg, about 131 mg, about 132 mg, about 133 mg, about 134 mg, about 135 mg, about 136 mg, about 137 mg, about 138 mg, about 139 mg, about 140 mg, about 141 mg, about 142 mg, about 143 mg, about 144 mg, about 145 mg, about 146 mg, about 147 mg, about 148 mg, about 149 mg, about 150 mg, about 151 mg, about 152 mg, about 153 mg, about 154 mg, about 155 mg, about 156 mg, about 157 mg, about 158 mg, about 159 mg, about 160 mg, about 161 mg, about 162 mg, about 163 mg, about 164 mg, about 165 mg, about 166 mg, about 167 mg, about 168 mg, about 169 mg, about 170 mg, about 171 mg, about 172 mg, about 173 mg, about 174 mg, about 175 mg, about 176 mg, about 177 mg, about 178 mg, about 179 mg, about 180 mg, about 181 mg, about 182 mg, about 183 mg, about 184 mg, about 185 mg, about 186 mg, about 187 mg, about 188 mg, about 189 mg, about 190 mg, about 191 mg, about 192 mg, about 193 mg, about 194 mg, about 195 mg, about 196 mg, about 197 mg, about 198 mg, about 199 mg, or about 200 mg or administering (e.g., orally) any range of amounts created by using two of the aforementioned amounts as endpoints. In some aspects, the method or use includes oral administration of 5 to 50 mg of Compound A in a single or divided doses. In some aspects, method or use includes the oral administration of a single or divided dose of 10, 20, or 25 mg of Compound A. In some aspects, the method or use includes oral administration of a single or divided dose of 20 mg of Compound A.

In some aspects, the methods and uses described herein, such as the method of or use in treating a depressive disorder in a human in need thereof, is achieved by administering (e.g., orally) at least 20 mg of Compound A, such as at least 25, 30, 35, 50, 75, or 100 mg of Compound A. In some embodiments, the methods and uses described herein, such as the method of or use in treating a depressive disorder in a human in need thereof, is achieved by administering (e.g., orally) at least 50 mg of Compound A per day, such as at least 60, 75, 85, 100, 125, 150, 175, or 200 mg of Compound A per day.

In some embodiments, the methods and uses described herein, such as the method of or use in treating a depressive disorder in a human in need thereof, is achieved by administering (e.g., orally) a therapeutically effective amount of Compound A per day, such as 5 to 1000 mg of Compound A per day, such as 5 to 500 mg or 5 to 250 mg of Compound A per day. For example, the method or use can include administering (e.g., orally) about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, or about 1000 mg of Compound A per day, or administering (e.g., orally) per day a range of amounts created by using two of the aforementioned amounts as endpoints. In some aspects, the method or use includes orally administering 10 to 200 mg of Compound A per day, such as 10, 15, 20, 25, 30, 35, or 40 mg to 75, 100, 125, 150, 175, or 200 mg of Compound A per day, including 20 to 150 mg per day. In some aspects, the oral administration includes 50, 75, 100, or 125 mg of Compound A per day, such as 100 mg per day.

In certain instances, the above daily doses of Compound A are administered (e.g., orally) as multiple doses per day, such as in two, three, four, or five doses per day. For Example, a daily dose of 100 mg, maybe administered in five 20 mg, four 25 mg, three 33.3 mg, or two 50 mg doses throughout the day.

In some embodiments, the above daily doses of Compound A are administered (e.g., orally) as a single dose. For example, about 5, 10, 15, 20, 25, or 30 mg to about 50, 65, 75, 100, 125, or 150 mg of Compound A per day can be orally administered as a single dose, including 10-25 mg, 10-30 mg, and 10-40 mg per day as a single dose, such as 10-25 mg per day as a single dose. Relatedly, any of the doses of Compound A discussed in the preceding paragraphs may be included in a unit dosage form.

In certain embodiments, the methods and uses described herein, when using the daily dosing disclosed herein, achieve a steady state for Compound A within 6 to 9 days, such as in about 1 week.

In additional embodiments, the above-discussed methods or uses of treating a depressive disorder by administering (e.g., orally) a therapeutically effective amount of Compound A comprises administration of Compound A to the human under fed conditions. In some embodiments, the oral administration of Compound A to a human under fed conditions (i.e., with food or in temporal proximity to the ingestion of food) significantly enhances the bioavailability and exposure of Compound A as compared to the oral administration of Compound A to the human under fasted conditions (i.e., without food or not in temporal proximity to the ingestion of food). In some embodiments, the oral administration of Compound A to a human under fed conditions increases one or more pharmacokinetic parameters for Compound A (e.g., $C_{max}$, $AUC_{inf}$, $T_{max}$, $t^{1/2}_{\lambda z}$, etc.) as compared to when the same amount of Compound A is orally administered to the human under fasted conditions.

In certain embodiments, the methods and uses described herein administer Compound A in the form of a pharmaceutically acceptable oral composition that comprises Compound A and one or more pharmaceutically acceptable carriers or excipients. The amount of Compound A included in these compositions may correspond to one or more of the amounts described herein. In some embodiments, the compositions are a unit dose.

Examples of pharmaceutically acceptable oral compositions that comprise Compound A include solid formulations (such as tablets, capsules, lozenges, dragées, granules, powders, wafers, multi-particulates, and films), liquid formulations (such as aqueous solutions, elixirs, tinctures, slurries, suspensions, and dispersions), and aerosolized formulations (such as mists and sprays). In one embodiment, a pharmaceutically acceptable oral composition of Compound A includes a pediatric suspension or granulate. All above-noted amounts of Compound A may be included in such formulations, e.g., a capsule comprising 5, 10, 15, 10, 25, 30, or 35 mg of Compound A.

In another embodiment, kits are provided for oral administration of Compound A for the treatment of a depressive disorder upon oral administration. Such kits comprise a plurality of oral dosage unit forms of Compound A in combination with instructions for orally administering of Compound A.

Additional embodiments and examples of the present disclosure are described herein. These embodiments and examples are illustrative and should not be construed as limiting the scope of the claimed invention.

5. EXAMPLES

Studies were conducted to determine the effect of Compound A in a rodent model of behavioral despair (i.e., mouse forced swim test). Further analysis determined the total brain-to-plasma ratio of Compound A in the forced swim test. Additional studies are conducted to determine the effect, if any, of Compound A in accepted models of depression.

5.1. Example 1. Mouse Forced Swim Test

Objective: A study was performed to assess the potential efficacy of Compound A using the mouse forced swim test. The forced swim test is a model of behavioral despair, and is sensitive to detection of various classes of antidepressant drugs (Can et al., The Mouse Forced Swim Test. J. Vis. Exp. 2012 (59), e3638, DOI:10.3791/3638).

Study Design: Forty (40) male CD-1 mice received a 1-week period of acclimation to the test facility prior to the commencement of testing (events summarized in Table 1). Animals were housed 5 per cage with unrestricted access to rodent chow and water (SOP ROD.03.01, SOP ROD.04.01, SOP ROD.18) and maintained on a 12 h/12 h light/dark cycle with all experimental activity occurring during the animals' light cycle. All animal use procedures were performed in accordance with the principles of the Canadian Council on Animal Care (CCAC).

TABLE 1

Summary of Study Events

| Study Day | Key Event | Procedure |
|---|---|---|
| −3 | Animal arrival | Acclimation to the animal facility |
| 0 | Forced swim test | General health observations and body weights Forced swim test Blood and brain collection (N = 20 animals dosed with Compound A) |

Formulation of Compound A: Compound A (99.4% pure) was weighed (no correction for purity) and dissolved in DMSO at 20× the intended final concentration. The 20×DMSO stock solution of Compound A was diluted 20 fold with 0.5% methyl cellulose in water to achieve the final desired concentration. When Compound A precipitated as a fine suspension, stirring or vortex mixing yielded a homogenous suspension. The above formulation was kept at room temperature and stirred continuously or vortex mixed prior to each dose administration. The test articles are summarized in Table 2.

TABLE 2

Test Articles

| Test Article | BEW | Dose | Route | Ptt[1] | Dose Volume | Vehicle |
|---|---|---|---|---|---|---|
| Compound A | 1 | 1 and 3 mg/kg | IP | 30 min | 10 mL/kg | 5% DMSO, 0.5% methyl cellulose[2] in reverse osmosis water; viscosity: 400 cP |
| Imipramine[3] | 1.13 | 30 mg/kg | IP | 30 min | 10 mL/kg | Saline |

[1]Pretreatment time.
[2]Sigma-Aldrich Catalog #M0430 (meets USP testing specifications).
[3]Imipramine is a known tricyclic antidepressant that can also reduce symptoms of agitation and anxiety.

Forced swim test: Forty (40) male CD-1 mice received the appropriate dose of the vehicle, test article, or positive control (treatments summarized in Table 3). Following a pre-determined pre-treatment time (Can et al., 2012), animals were gently placed into tall glass cylinders filled with water (20-25° C.). After a period of vigorous activity, the mouse adopted a characteristic and readily identifiable immobile posture. The swim test involved scoring the duration of immobility. Over a 6-minute test session, the latency to first immobility was recorded (in seconds). The duration of immobility (in seconds) during the last 4 minutes of the test was also measured. Activity or inactivity from 0-2 minutes was not recorded.

TABLE 3

Summary of Treatment Groups

| Group | Treatment | Route | Ptt | Dose Volume | Group Size |
|---|---|---|---|---|---|
| A | Vehicle | IP | 30 min | 10 mL/kg | N = 10 |
| B | Compound A (1 mg/kg) | IP | 30 min | 10 mL/kg | N = 10 |
| C | Compound A (3 mg/kg) | IP | 30 min | 10 mL/kg | N = 10 |
| D | Imipramine (30 mg/kg) | IP | 30 min | 10 mL/kg | N = 10 |

Figure 1:
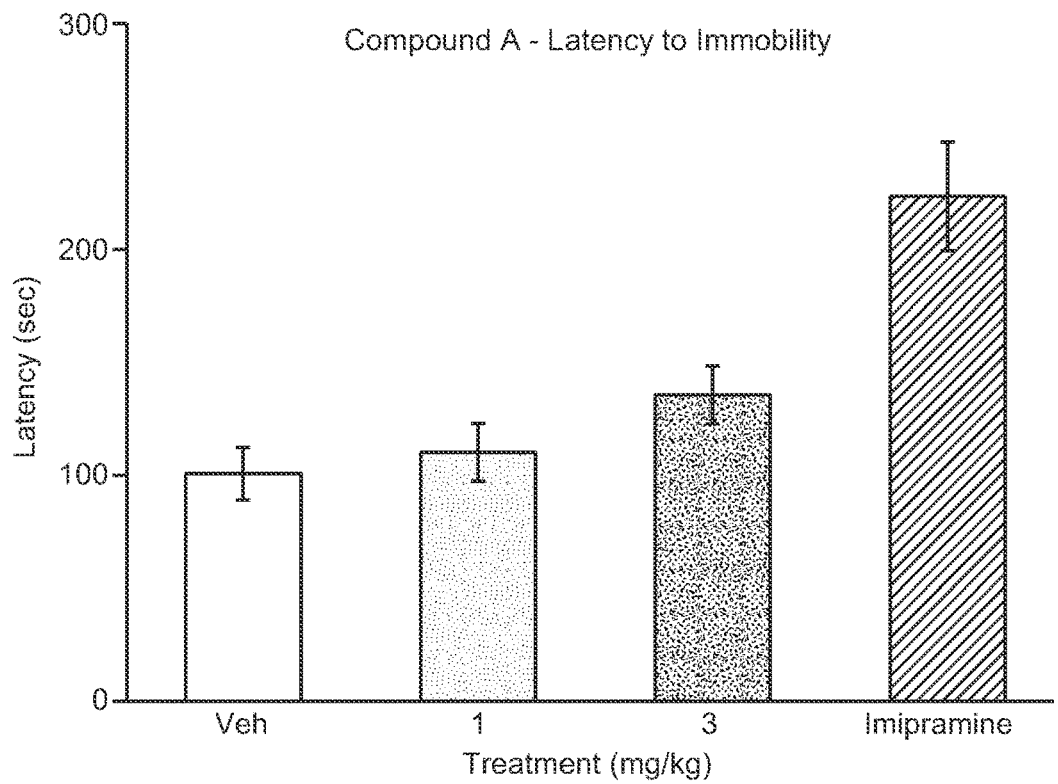
FIG. 1 shows results of the mouse forced swim test including a graphical representation of the average time of latency (sec, y-axis) to immobility for vehicle, 1 mg/kg Compound A, 3 mg/kg Compound A, and imipramine dosing (x-axis).
Figure 2:
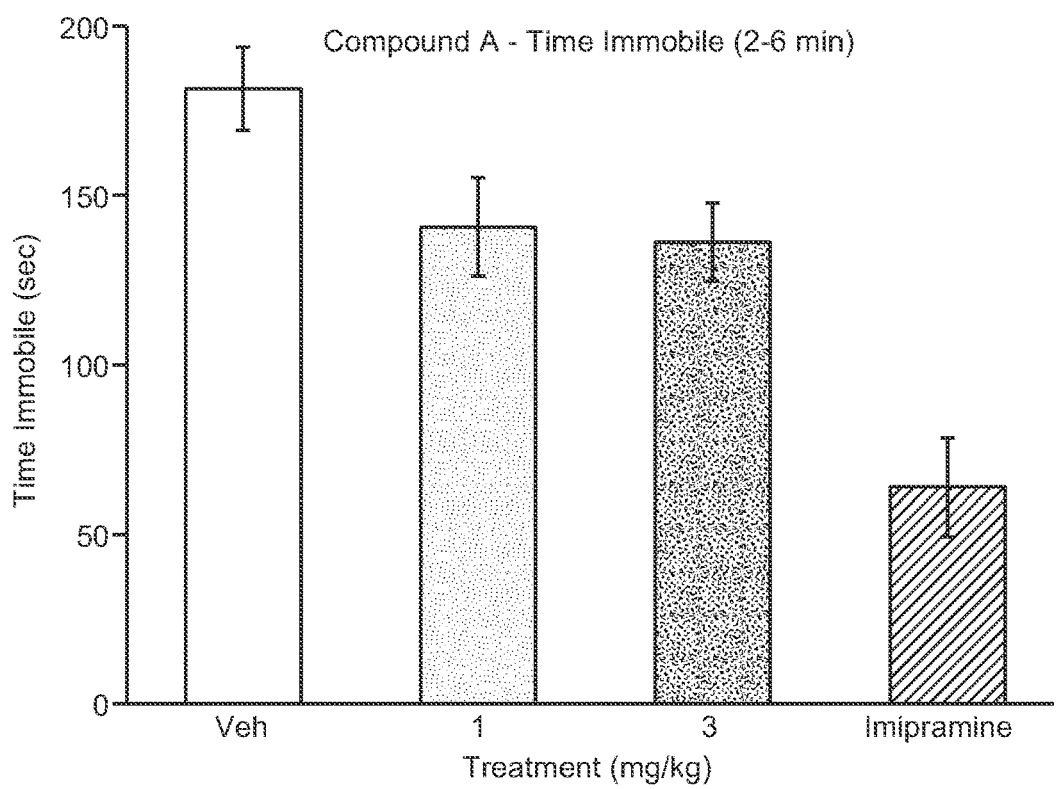
FIG. 2 shows results of the mouse forced swim test including a graphical representation of the average time immobile (2-6 min)(sec, y-axis) for vehicle, 1 mg/kg Compound A, 3 mg/kg Compound A, and imipramine dosing (x-axis).
Figure 3:
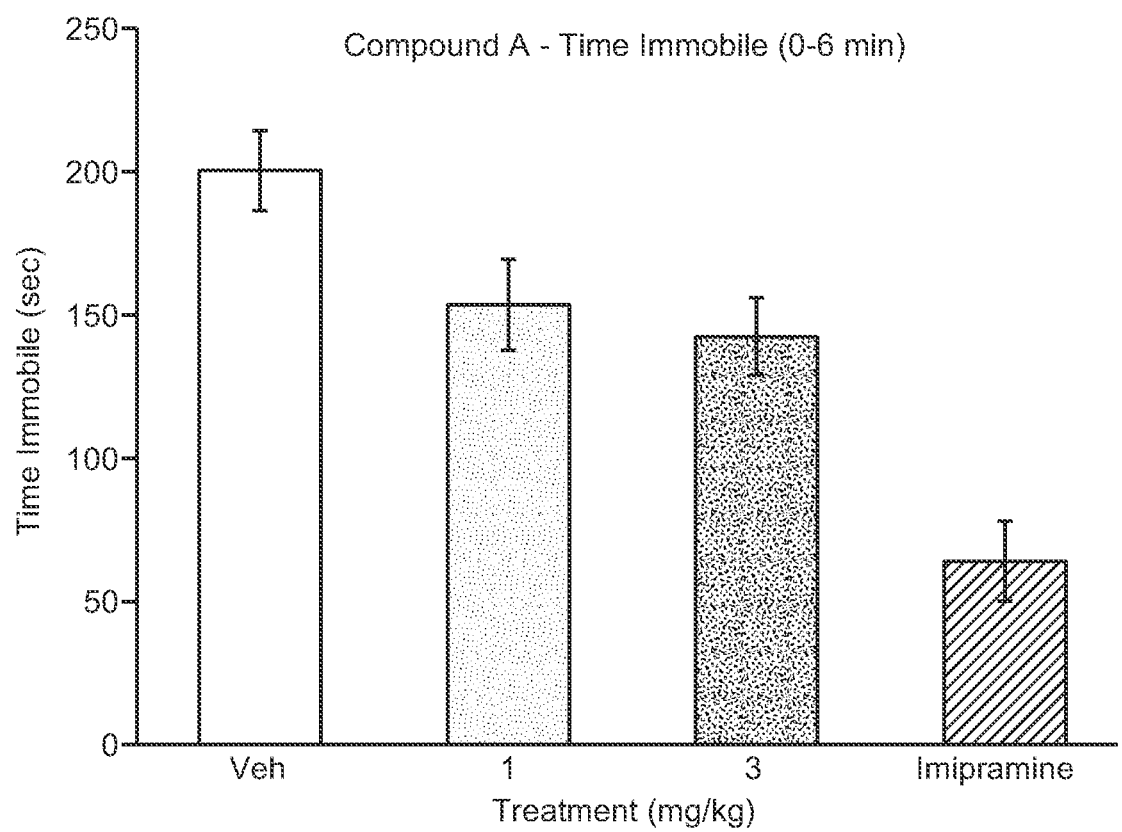
FIG. 3 shows results of the mouse forced swim test including a graphical representation of the average time immobile (0-6 min)(sec, y-axis) for vehicle, 1 mg/kg Compound A, 3 mg/kg Compound A, and imipramine dosing (x-axis).

Results: Results of the forced swim test are shown in Table 4 and FIGS. 1-3.

TABLE 4

Results of the Forced Swim Test

| | | | Latency to | Time Immobile (sec) | | |
|---|---|---|---|---|---|---|
| Group | ID | Treatment | Immobility (sec) | 0-2 min | 2-6 min | 0-6 min |
| A | A1 | Vehicle | 80 | 39 | 222 | 261 |
| | A2 | | 106 | 13 | 226 | 239 |
| | A3 | | 200 | 0 | 188 | 188 |
| | A4 | | 79 | 38 | 209 | 247 |
| | A5 | | 91 | 22 | 119 | 141 |
| | A6 | | 90 | 20 | 148 | 168 |
| | A7 | | 99 | 20 | 190 | 210 |
| | A8 | | 91 | 5 | 199 | 204 |
| | A9 | | 79 | 15 | 121 | 136 |
| | A10 | | 93 | 24 | 192 | 216 |
| | Average | | 100.8 | 19.6 | 181.4 | 201.0 |
| | Standard Deviation | | 11.4 | 3.9 | 12.3 | 13.6 |
| B | B1 | Compound A (1 mg/kg) | 77 | 32 | 142 | 174 |
| | B2 | | 84 | 28 | 170 | 198 |
| | B3 | | 206 | 0 | 33 | 33 |
| | B4 | | 100 | 16 | 109 | 125 |
| | B5 | | 70 | 20 | 149 | 169 |
| | B6 | | 109 | 4 | 192 | 196 |
| | B7 | | 144 | 0 | 134 | 134 |
| | B8 | | 105 | 7 | 189 | 196 |
| | B9 | | 130 | 0 | 141 | 141 |
| | B10 | | 80 | 20 | 150 | 170 |
| | Average | | 110.5 | 12.7 | 140.9 | 153.6 |
| | Standard Deviation | | 13.0 | 3.8 | 14.4 | 15.8 |
| C | C1 | Compound A (3 mg/kg) | 135 | 0 | 166 | 166 |
| | C2 | | 165 | 0 | 144 | 144 |
| | C3 | | 155 | 0 | 122 | 122 |
| | C4 | | 86 | 23 | 184 | 207 |
| | C5 | | 150 | 0 | 82 | 82 |
| | C6 | | 127 | 0 | 146 | 146 |
| | C7 | | 192 | 0 | 101 | 101 |
| | C8 | | 162 | 0 | 90 | 90 |
| | C9 | | 83 | 21 | 163 | 184 |
| | C10 | | 105 | 15 | 166 | 181 |
| | Average | | 136.0 | 5.9 | 136.4 | 142.3 |
| | Standard Deviation | | 11.3 | 3.1 | 11.3 | 13.5 |
| D | D1 | Imipramine (30 mg/kg) | 224 | 0 | 32 | 32 |
| | D2 | | 213 | 0 | 45 | 45 |
| | D3 | | 180 | 0 | 63 | 63 |
| | D4 | | 169 | 0 | 133 | 133 |
| | D5 | | 215 | 0 | 84 | 84 |
| | D6 | | 350 | 0 | 10 | 10 |
| | D7 | | 163 | 0 | 126 | 126 |
| | D8 | | 244 | 0 | 42 | 42 |
| | D9 | | 360 | 0 | 0 | 0 |

TABLE 4-continued

Results of the Forced Swim Test

| Group | Animal ID | Treatment | Latency to Immobility (sec) | Time Immobile (sec) | | |
|---|---|---|---|---|---|---|
| | | | | 0-2 min | 2-6 min | 0-6 min |
| | D10 | | 126 | 0 | 102 | 102 |
| | Average | | 224.4 | 0.0 | 63.7 | 63.7 |
| | Standard Deviation | | 24.3 | 0.0 | 14.7 | 14.7 |

Statistical Analysis: The results in Table 4 were tested for significance using T-, univariate, and Dunnett's tests as shown in Tables 5-14.

TABLE 5

T-tests for Latency to Immobility Results

| | Vehicle | 1 mg/kg | 3 mg/kg | Imipramine |
|---|---|---|---|---|
| | 80 | 77 | 135 | 224 |
| | 106 | 84 | 165 | 213 |
| | 200 | 206 | 155 | 180 |
| | 79 | 100 | 86 | 169 |
| | 91 | 70 | 150 | 215 |
| | 90 | 109 | 127 | 350 |
| | 99 | 144 | 192 | 163 |
| | 91 | 105 | 162 | 244 |
| | 79 | 130 | 83 | 360 |
| | 93 | 80 | 105 | 126 |
| T-test (1 tail) | | 0.290 | 0.021 | 0.000 |
| T-test (2 tail) | | 0.581 | 0.042 | 0.000 |

TABLE 6

Univariate Tests of Significance for Latency to Immobility Results (Guadalupe)

Sigma-restricted parameterization
Effective hypothesis decomposition;
Std. Error of Estimate 50.44372

| Effect | SS | Degr. Of Freedom | MS | F | P |
|---|---|---|---|---|---|
| Intercept | 817102.2 | 1 | 817102.2 | 321.1161 | 0.000000 |
| Treatment | 95120.3 | 3 | 31706.8 | 12.4606 | 0.000010 |
| Error | 91604.5 | 36 | 2544.6 | | |

TABLE 7

Dunnett's Test for Latency to Immobility Results (Guadalupe)

Probabilities for Post Hoc Tests (2-sided)
Error: Between MSE = 2544.6, df = 36.000

| Cell No. | Treatment | {1} 100.80 |
|---|---|---|
| 1 | Vehicle | |
| 2 | 1 mg | 0.949581 |
| 3 | 3 mg | 0.290085 |
| 4 | Imipramine 30 mg | 0.000018 |

TABLE 8

T-tests for 2-6 min Results

| | Vehicle | 1 mg/kg | 3 mg/kg | Imipramine |
|---|---|---|---|---|
| | 222 | 142 | 166 | 32 |
| | 226 | 170 | 144 | 45 |
| | 188 | 33 | 122 | 63 |
| | 209 | 109 | 184 | 133 |
| | 119 | 149 | 82 | 84 |
| | 148 | 192 | 146 | 10 |
| | 190 | 134 | 101 | 126 |
| | 199 | 189 | 90 | 42 |
| | 121 | 141 | 163 | 0 |
| | 192 | 150 | 166 | 102 |
| T-test (1 tail) | | 0.023 | 0.007 | 0.000 |
| T-test (2 tail) | | 0.046 | 0.015 | 0.000 |

TABLE 9

Univariate Tests of Significance for 2-6 min Results (Guadalupe)

Sigma-restricted parameterization
Effective hypothesis decomposition;
Std. Error of Estimate 41.83426

| Effect | SS | Degr. Of Freedom | MS | F | P |
|---|---|---|---|---|---|
| Intercept | 682254.4 | 1 | 682254.5 | 389.8361 | 0.000000 |
| Treatment | 71959.8 | 3 | 23986.6 | 13.7058 | 0.000004 |
| Error | 63003.8 | 36 | 1750.1 | | |

TABLE 10

Dunnett's Test for 2-6 min Results (Guadalupe)

Probabilities for Post Hoc Tests (2-sided)
Error: Between MSE = 1750.1, df = 36.000

| Cell No. | Treatment | {1} 181.40 |
|---|---|---|
| 1 | Vehicle | |
| 2 | 1 mg | 0.093513 |
| 3 | 3 mg | 0.055570 |
| 4 | Imipramine 30 mg | 0.000008 |

TABLE 11

T-tests for 0-6 min Results

| | Vehicle | 1 mg/kg | 3 mg/kg | Imipramine |
|---|---|---|---|---|
| | 261 | 174 | 166 | 32 |
| | 239 | 198 | 144 | 45 |
| | 188 | 33 | 122 | 63 |
| | 247 | 125 | 207 | 133 |
| | 141 | 169 | 82 | 84 |
| | 168 | 196 | 146 | 10 |
| | 210 | 134 | 101 | 126 |
| | 204 | 196 | 90 | 42 |
| | 136 | 141 | 184 | 0 |
| | 216 | 170 | 181 | 102 |
| T-test (1 tail) | | 0.018 | 0.003 | 0.000 |
| T-test (2 tail) | | 0.035 | 0.007 | 0.000 |

TABLE 12

Univariate Tests of Significance for 0-6 min Results (Guadalupe)

Sigma-restricted parameterization
Effective hypothesis decomposition;
Std. Error of Estimate 45.57429

| Effect | SS | Degr. Of Freedom | MS | F | P |
|---|---|---|---|---|---|
| Intercept | 785680.9 | 1 | 785680.9 | 378.2738 | 0.000000 |
| Treatment | 97328.5 | 3 | 32442.8 | 15.6199 | 0.000001 |
| Error | 74772.6 | 36 | 2077.0 | | |

TABLE 13

Dunnett's Test for 0-6 min Results (Guadalupe)

Probabilities for Post Hoc Tests (2-sided)
Error: Between MSE = 2077.0, df = 36.000

| Cell No. | Treatment | {1} 201.00 |
|---|---|---|
| 1 | Vehicle | |
| 2 | 1 mg | 0.066283 |
| 3 | 3 mg | 0.018039 |
| 4 | Imipramine 30 mg | 0.000008 |

Table 5-13 shows that Compound A shows statistically significant effects in the mouse forced swim test model. For example, the 3 mg/kg dose gave a 2-tailed T-test score of 0.042, 0.015, and 0.007 (e.g., <0.05) for the latency to immobility, 2-6 min, and 0-6 min results respectively.

Blood and Brain Collection: Immediately following the forced swim test, all animals dosed with test article were anesthetized with isoflurane inhalant, and terminal blood collection (~1 ml) was performed via cardiac puncture into potassium EDTA blood collection tubes (SOP ROD.14.02). Plasma was isolated from whole blood by centrifugation at 3000 rpm at 4° C. for 5 minutes. Once isolated, plasma was placed in cryovials and frozen at −80° C. until shipment for bioanalysis. Following blood collection, animals were decapitated and the whole brain collected as per standard operating procedure (SOP ROD.59). Brains were weighed, flash frozen, and stored at −80° C. until shipment. Blood and brain concentrations of Compound A are shown in FIG. 4. The total brain-to-plasma ratio (B/P ratio) of 2.2 for both 1 and 3 mg/kg doses suggests good CNS penetration in vivo.

5.2. Example 2. Tail Suspension Test

The tail suspension test (TST) has become one of the most widely used models for assessing antidepressant-like activity in mice. The test is based on the fact that animals subjected to the short-term, inescapable stress of being suspended by their tail, will develop an immobile posture. The protocol is described in Cryan, J. F. et al., Neurosci. Biobehav. Rev. 2005, 29:571-625.

Description: The apparatus consists of two suspension units of three cages each and enables six mice to be tested simultaneously. Each mouse is suspended by the tail using adhesive tape to a hook connected to a strain gauge. The strain gauge picks up all movements of the mouse and transmits these to a central unit, which digitalizes the signals. The signals are displayed visually using LEDs, which permit on-line verification of the good functioning of each unit. Included in the central unit is a level filtering device (from 1 to 9), which can be set to the desired sensitivity to provide maximum discrimination of gross body movements from other micro-movements of the animals or its internal organs.

Parameters: The "duration of immobility" is the main parameter measured. This is calculated from the cumulated time during which the animals movements do not exceed the threshold determined by the level filtering device. The "energy" expended by the animal during the test is measured by cumulated amplitudes of individual movements in arbitrary units. The "power of the movements" is calculated from the total energy expended by the animal during the test, divided by the total time the animal is active (arbitrary units). For all three parameters, a computer provides data collection, generation of experimental schedule (randomization) and groupings of results (means, medians and SEM are automatically calculated for each treatment group).

Procedure: On the test day, mice are moved from the housing colony room to the testing laboratory (cages are covered with a filter during the transport), where the filter coverage is immediately removed and where mice stay undisturbed for at least 1 h before testing. Mice are then treated with drug, and then after 1 h (PO) or 30 min (IP) of treatment, the mice are suspended by the tail (e.g., with adhesive tape) in the TST apparatus according to a randomization scheme. The test lasts 6 min to obtain the measurements for all three parameters. Experiments are carried out between 08:00 and 12:30. Typically, 12 mice per treatment-group are used.

Drug Treatment: Compound A and imipramine are formulated and administered at the concentrations described in Table 2 of Example 1 above and dosed 30 min before the TST. For each experiment, at least one control group is included, handled, and tested in parallel under strictly identical experimental conditions.

Statistics: For each experiment, the statistical significance for the parameter "immobility time" is assessed using one way analysis of variance (ANOVA), followed when appropriate by a post-hoc analysis using the Dunnett's test. If the parameters "energy" and "power of movements" test of normality fails, inter-group comparisons are performed using Kruskal-Wallis one way analysis of variance on ranks followed, when appropriate, by a post-hoc analysis using the Dunn's test. For all three parameters, values of p<0.05 are considered as statistically significant.

5.3. Example 3. Sucrose Preference and Intracranial Self-Stimulation

Sucrose intake and intracranial self-stimulation (ICSS) are hedonic measures for chronic mild stress (CMS) induced behavioral deficits in rodents. The protocol is described in Nielsen, C. K. et al., Behav. Brain Res. 2000, 107:21-33. A study is performed to assess the potential efficacy of Compound A using the CMS model.

Subjects: Male Wistar rats and male Pieball Virol Glaxo (PVG) hooded rats weighing 250-300 and 220-240 g, respectively, at the beginning of the study, are used. The rats are housed individually or in pairs in polycarbonate cages and maintained on a 12 h light:dark cycle (lights on 06:00). Except when required by the test, the animals have free access to food and water. Temperature (22±1° C.), relative humidity (55±5%) and air exchanges (16 times per h) are automatically controlled. Body weight is measured weekly during all experiments.

Drug Treatment: Compound A and imipramine are formulated and administered at the concentrations described in Table 2 of Example 1 above on a daily basis during the stress regimes and/or intracranial self-stimulation. For each experiment, at least one control group is included, handled, and tested in parallel under strictly identical experimental conditions.

Stress Regimes: Two different stress regimes (CMS-1 and CMS-2) are used. Each week of CMS-1 consists of two periods (8 and 19 h) of food deprivation; three periods (6, 7, and 19 h) of water deprivation; 2 periods (7 and 16 h) of cage tilt (45°); two 17 h periods of paired housing; one 17 h period in a soiled cage (200 ml water in 100 g sawdust bedding); one 6 h period of low intensity stroboscopic illumination (150 flashes:min); and 48 h of light:dark reversal. Each week of CMS-2 consists of one 17 h period of food and water deprivation immediately followed by 2 h of restricted access to food; one 17 h period of water deprivation immediately followed by 1 h exposure to an empty bottle; one 17 h periods of paired housing in a soiled cage (200 ml water in 100 g sawdust bedding); eight 1 h periods of confinement to small cages (25×10×10 cm); one period of overnight illumination; and 64 h of reversed light:dark cycle during the weekend.

5.3.1 Hedonic Measures

Sucrose Intake: Rats (Wistar rats for some experiments and PVG hooded rats for other experiments) are acquired twice weekly (Tuesday and Friday) to consume a 1% sucrose solution. The acquisition consists of 8-10 1 h baseline tests in which sucrose solution is presented, in their home cage, following a 20 h period of food and water deprivation. Sucrose intake is measured by weighing the bottles before and after the test. Following stable baseline levels, sucrose consumption is measured during the CMS protocol, under similar conditions, at weekly intervals (Wednesday), throughout the experiments. The food and water deprivation prior to the sucrose tests is a stressor upon which subsequent stressors included in the CMS regime is imposed, a prior stressor history which is not considered in any subsequent analysis.

Intracranial Self-Stimulation: Rats (Wistar rats for some experiments and PVG hooded rats for other experiments) are housed in pairs and allowed 2 weeks to acclimatize before surgery. They are anesthetized and mounted in a stereotaxic frame with the incisor bar set 2.7 mm below the interaural line. Stainless-steel bipolar electrodes are implanted unilaterally into the ventral tegmental area (VTA) with the electrode tips separated by 0.5 mm. The coordinates used are 3.2 mm anterior to the interaural line, 0.6 mm lateral from the midline and 8.2 mm ventral from the skull surface. Five stainless-steel screws and dental cement are used to anchor the electrode assembly to the skull. Two weeks postoperatively each rat is trained to make a nose-poke for rewarding intracranial electrical stimulation in a test chamber placed in a sound-attenuated box. Poking the nose into a hole (2.5 cm in diameter) located in the side wall 1 cm above the floor interrupts a convergent light beam, thereby initiating brain stimulation delivered through a constant current stimulator. Each nose-poke produces a 0.5 s train of monophasic square-wave pulses, each of 0.1 ms in duration. Stimulation is delivered under a fixed-interval 1 s schedule of reinforcements in order to avoid extreme density of stimulation. Electrical stimulation and data recording are controlled through a computer and interface. The rats are initially trained at a fixed stimulation frequency of 70 Hz and an individually selected current intensity (70-300 mA) in order to maintain the highest possible response rate without inducing motor impairment. They are trained daily in 40 min sessions for approximately 3 weeks. Subsequently, rate-frequency curves are established by stepwise changing the frequency while maintaining the current intensity constant. At 2 min intervals the frequency is decreased and then increased in 0.05-0.2 log unit steps in the range 1.1-1.9 log Hz (10-85 Hz). Each session comprises 15 discrete 2-min trials for each frequency with 1 priming stimulation at the beginning of each trial. The decreasing series of frequencies is used as a warm up phase; that is; only data obtained from the ascending phase is used in the subsequent calculations. The increasing series of frequencies are individually selected so as to yield an ascending curve with at least two adjacent points at maximum and minimum response rate, respectively. This study employs the rate-frequency version of the curve-shift method to assess CMS effect on reward. The properties of the rate-frequency function, in particular with regard to separating ICSS reward effects on operant motor:performance capacity, have been extensively validated and investigated. ICSS behavior is evaluated by determining the frequency that will support 50% of maximal response rate, the effective frequency ($EF_{50}$). Based on the "broken-line" principle a mathematical model to estimate EF50 is described. This method gives reliable and stable $EF_{50}$ estimations. Each test day ascending rate-frequency curves are generated for each rat by modelling the observed response rate (nosepokes (NP):2 min trial) as a function of log 10 of the imposed frequency (F). The function consists of three linear segments; a horizontal lower asymptote through the minimum response ($NP_{min}$), a horizontal upper asymptote through the maximum response ($NP_{max}$) and a linear transition between the asymptotes (a+b*F). Only data (M) between the last $NP_{min}$ and first $NP_{max}$ is included. This can be described by the following equations:

1. Consider $M=\{(F, NP(F)|max\{F|NP(F) =NP_{min}\}\leq F\leq min\{F|NP(F) NP_{max}\}\}|$
2. Fit f(F) min(max(a+b*F, $NP_{min}$), $NP_{max}$) to the data in M by the least squares procedure. In case of ambiguity, the function with the smallest b is used.

The effective frequency ($EF_{50}$), defined as the frequency that will support 50% of the maximal response rate is determined. A lateral curve-shift along the axis of simulation frequencies, i.e., a change in $EF_{50}$, will reflect changes in reward effectiveness of the stimulation. Rate-frequency testing is performed twice weekly (Tuesday and Friday). A stable response is achieved when maximum response showed no increasing or decreasing trends and when $EF_{50}$ varied by less than 10-12%. The animals are subsequently allocated to two matched groups.

5.3.2 Design of Experiments

The effects on sucrose intake in Wistar rats exposed to the CMS-1 regime (see above): Wistar rats are brought into the laboratory 4 weeks before the experiment was started. Except when required by the stress protocol the animals are individually housed. According to baseline sucrose intakes the animals are allocated to two matched groups. One group of rats is subjected to CMS-1 for a period of 6 weeks, while the other group is maintained under standard laboratory conditions.

The effects on sucrose intake in PVG hooded rats exposed to the CMS-1 regime (see above): PVG hooded rats are brought into the laboratory 3 weeks before the experiment was started. Except when required by the stress protocol the animals are individually housed. According to baseline sucrose intakes the animals were allocated to two matched groups. One group of rats is subjected to CMS-1 for a period of 9 weeks, while the other group is maintained under standard laboratory conditions.

The effects on ICSS in Wistar rats exposed to the CMS-2 regime (see above): Wistar rats are allocated to one group, housed individually and submitted to 10 weeks of CMS-2 and another group (control group), paired housed under standard laboratory conditions. Their $EF_{50}$ are determined twice weekly and comparisons with the mean of the two last baseline tests are performed for each individual rat.

The effects of rat strain and stress regime on ICSS behavior (see above): Wistar rats are allocated to three matched groups; a control group and two groups subjected to 9 weeks of CMS-1 and CMS-2, respectively. PVG rats are allocated to two matched groups; one group is submitted to 9 weeks of CMS-2 and the other group (control group) maintained under standard laboratory conditions. The control groups are housed in pairs. Except where required by the stress protocol the rats in the stress groups are singly housed. Their $EF_{50}$ are determined twice weekly and comparisons with the mean of the two last baseline tests are performed for each individual rat.

Histology: After completion of ICSS testing, the animals are killed and the brains removed and stored at 80° C. Sections of 12 mm are cut on a cryostat before being stained with cresyl violet. Electrode tip placement is determined on the frontal planes of the Paxinos and Watson stereotaxic atlas.

Statistical Analysis: In addition to comparisons of either normality or variance homogeneity between the control group and stress group tests, both for sucrose intake and ICSS data, the data may also be evaluated by non-parametric statistics. Two way analysis of variance (ANOVA) are performed on ranks, with days and treatment (stress) as factors and with animal nested in treatment which implies that a set of parameters corresponds to only one observation. All observations are, therefore, independent. In the ICSS experiments, there may be a sub-classification of the stress group. If the total mean response of a stressed animal exceeds the maximum mean response in the control group, it is classified as belonging to a subgroup. Prior to comparisons between stress (sub- and main group) and control group the response of the stress subgroup and the main group are compared by two-way ANOVA on ranks, with days and group as factors and with animal nested in groups. Significant main effects ($p<0.05$) on treatment are followed by an unpaired t-test for each day. For clarity, both sucrose intake data and ICSS data may be presented as mean±SEM, still performing non-parametric analysis. Body weight data that passes normality and variance homogeneity tests are analyzed by one or two way ANOVA. Multiple comparisons are performed by Tukey's test and/or Kruskal-Wallis ANOVA on ranks are used.

5.4. Example 4. Novelty-Induced Hypophagia

The inhibition of feeding produced by novelty, termed 'hyponeophagia', provides an anxiety-related measure that is sensitive to the effects of chronic, but not acute or subchronic, antidepressant treatment. The protocol is described in Dulawa, S. C. and Hen, R., Neurosci. Biobehav. Rev. 2005, 29:771-83.

Subject Selection: Male Balb/cJ mice are maintained on a 12 L:12 D schedule (lights on at 06:00) and are housed in groups of five with same-type mice. Food and water are provided ad libitum. Behavioral testing occurred during the light phase between 07:00 and 17:00.

Apparatus and Procedure: Compound A and imipramine are formulated and administered at the concentrations described in Table 2 of Example 1 above, applied at least 30 min before testing. Compound A plasma levels are determined by liquid chromatography with fluorescence detection.

Chronic Testing: Male Balb/cJ mice are dosed (e.g., 1 and 3 mg/kg per day Compound A). Separate groups of mice are used for sub-chronic vs. chronic experiments. On day 23 of treatment, mice are singly housed. Mice are trained to drink sweetened condensed milk for three consecutive days (days 25-27). Mice are presented with diluted sweetened condensed milk (1:3; milk:water) for 30 min each day. Milk is presented in 10 ml serological pipettes with sippers attached with Parafilm. Pipettes are closed with rubber stoppers and positioned through wire cage lids. Home cage testing occurs on day 28 when mice are briefly removed from their cages to position pipettes containing milk, and testing begins when mice are returned to their cages. The latency to drink, and the volume consumed are recorded every 5 mm for 30 min. Home cage testing occurs under dim lighting (approx. 50 lux). Novel cage testing occurs on day 29, when mice are placed into new clean cages of the same dimensions but without shavings, with pipettes containing the milk positioned. Novel cage testing occurs under bright lighting (approx. 1200 lux), with white paper placed under cages to enhance aversiveness. Mice that never drank during the 30 min of home cage testing are eliminated from the experiment for presumably never learning to drink the milk during training. Sub-chronic testing is conducted using a separate group of male Balb/cJ mice are dosed (e.g., 1 and 3 mg/kg per day Compound A). Mice are singly housed, and then are trained to drink the milk beginning on day 1 of treatment. Mice are trained to drink the sweetened-condensed milk on days 1-3. They are then tested in the novelty-induced hypophagia test after 4 (home) and 5 (novel) days of sub-chronic treatment.

5.5. Example 5. Learned Helplessness Model

The learned helplessness paradigm is a depression model in which animals are exposed to unpredictable and uncontrollable stress, e.g., electroshocks, and subsequently develop coping deficits for aversive but escapable situations. The protocol is described in Chourbaji, S. et al., Brain Res. Protoc. 2005, 16:70-8.

Materials: The shock procedure is applied in a transparent plexiglass shock chamber ($18\times18\times30$ cm$^3$), equipped with a stainless steel grid floor (diameter of each grid: 0.5 cm, spacing: 0.6 cm). The two-way avoidance test is conducted in a two compartment shuttle box, equipped with infrared-light beams at the bottom of each of the two compartments to monitor spontaneous shuttling as well as behavioral responses to a light (conditioned) or an aversive footshock (unconditioned) stimulus, respectively. The shuttle box consists of equal sized compartments ($18\times18\times30$ cm$^3$) that are separated by a small gate (6 cm wide and 7 cm high). Both compartments of the shuttle box contain a grid floor (diameter of each grid: 0.5 cm, distance: 0.6 cm), through which the current is applied, and a signaling light at the top of each compartment. Protocol charts for both the shock procedure and shuttle box testing, respectively, are designed.

Hotplate: To exclude altered pain sensitivity as a confounding factor, all mice are tested on a hotplate.

Pharmacological Treatment: The model is pharmacologically validated with Compound A and imipramine formulated and administered at the concentrations described in Table 2 of Example 1 above, applied at least 30 min before testing. The capacity of Compound A is accessed to revert helpless behavior in the shuttle box.

Animals: 10-week-old male C57BL/6N mice are purchased and acclimatized to single housing in polycarbonate cages (type II) at constant conditions with a 12 h dark-light cycle and an average room temperature of 22° C. for 2 weeks prior to the experiments, with food and water ad libitum.

Inescapable Shock Procedure:
1. Mice are exposed to inescapable shocks during their active (dark) phase. Animals are transported in their home cages to the experimental room, and are then placed into the shock chamber.
2. The shock procedure comprises 360 scrambled foot shocks (0.150 mA) on two consecutive days. The foot shocks are unpredictable with varying duration (1-3 s) and interval-episodes (1-15 s), amounting to a total session duration of approximately 52 min. During the shock exposure, lights are turned off
3. Control animals undergo the same handling and contextual procedures without receiving the foot shocks. By thorough cleaning with 70% ethanol, care is taken that control animals, which do not receive electroshocks, are exposed to the shock chambers without being distressed by the smell of shocked mice. Daily cleaning with soap prevents fixation of potential alarm substances.

Assessment of Learned Helplessness: 24 h after the second shock procedure, learned helplessness is assessed in the dark phase of the animals by testing shuttle box performance. Each trial starts with a light stimulus of 5 s, announcing a subsequent foot shock of maximum 10 s duration (intensity: 0.150 mA). The intertrial interval is 30 s. The following behavioral reactions are defined: "avoidance" as adequate reaction to the light stimulus by changing to the other compartment immediately, "escape" as shuttling to the other compartment as reaction to the electric shock, and "failure" when no attempt to escape is made. Furthermore, the parameter escape latency is recorded as the time needed to shuttle into the other compartment after onset of the foot shock. For determination of the general activity, the shuttles before the first foot shock (initial activity), as well as the activity in-between the trials (intertrial interval activity or ITI) are recorded. Total time of testing for helplessness lasts about 20-24 min, the exact time period depending on the animal's ability to learn the paradigm and to respond properly. Before each trial, the apparatus is thoroughly cleaned with 70% ethanol. To underscore the assessment of "true" learned helplessness effects, which relies on the uncontrollability of the stress, an additional cohort of animals are tested for immunization. These animals are exposed to a pre-session, identical to the learned helplessness test in the shuttle box, in which they experience a controllable shock condition. Moreover, initial activity during the pre-exposure is monitored.

Pain Sensitivity: To exclude potential artifacts by altered pain sensitivities, which could influence the effect of the electroshocks, a subgroup of mice is tested on the hotplate prior to the learned helpless procedure at a temperature of 52° C. The latency to first reaction (jumping or licking the hind paws) is monitored.

Defining Helplessness: Following the evaluation of the behavioral parameters, the shocked animals are classified as "helpless" or "resistant", depending on their performance in the shuttle box test. Failures and escape latencies are taken as indicators for helplessness, and a k-means (k=2) clustering algorithm is applied to a data pool of mice subjected to the described protocol. The number of failures and the escape latencies are used as performance scores of the individual animals, because these are the most commonly reported indices of helplessness. These behavioral indices are normalized (i.e., transformed to Z scores) to prevent differences in the range of each variable, which could produce a bias, and then inadvertently be used to implement a clustering process. This classification is further refined by means of a two-step discriminant-canonical analysis, which also provides classification equations for identification of helpless/non-helpless mice following this protocol.

Pharmacological Validation: Additional C57BL/6N mice are trained and tested in the protocol. Prior to any pharmacological treatment, these mice are classified as "helpless" or "non-helpless" using the classification equations previously obtained (e.g., defining helplessness above) which takes into account the number of failures and the latency to escape. The duration of helplessness for approximately 10 days dictated a short-timed, Compound A treatment interval of 5-6 days. Thus, the animals undertake 5 days of a Compound A regimen. On day 6, animals are retested in the protocol. The classification equations are used again to classify each subject, but now the values of the retest session are used in for the calculation. The changes in this categorical classification (i.e., mice moving from "helpless" to "non-helpless" group) after Compound A treatment are considered as an index of sensitivity of the provided operational definition of helplessness. The analysis is complemented by the assessment of variations in the squared Mahalanobis distance to the centroid of the non-helpless group before/after the pharmacological treatment to have a continuous rather than categorical index of Compound A effects.

All of the U.S. patents, U.S. patent application publications, U.S. patent applications, foreign patents, foreign patent applications, and non-patent publications referred to in this specification are incorporated herein by reference in their entireties, including U.S. provisional application No. 62/932,724 filed Nov. 8, 2019.

Although the foregoing compositions, methods, and uses have been described in some detail to facilitate understanding, it will be apparent that certain changes and modifications may be practiced within the scope of the appended claims. Accordingly, the described embodiments are to be considered as illustrative and not restrictive, and the claimed invention is not to be limited to the details given herein, but may be modified within the scope and equivalents of the appended claims.

What is claimed is:

1. A method of treating a depressive disorder in a human in need thereof, comprising administering a therapeutically effective amount of Compound A to the human;
   wherein Compound A is N-[4-(6-fluoro-3,4-dihydro-1H-isoquinolin-2-yl)-2,6-dimethylphenyl]-3,3-dimethylbutanamide;
   wherein Compound A is orally administered to the human under fed conditions.

2. The method of claim 1, wherein Compound A is orally administered to the human between about 30 minutes prior to about 2 hours after eating a meal.

3. The method of claim 2, wherein Compound A is orally administered to the human during a meal or within 15 minutes after eating a meal.

4. The method of claim 1, wherein the method comprises enhancing the opening of a Kv7 potassium channel in the humam.

5. The method of claim 4, wherein the Kv7 potassium channel is one or more of Kv7.2, Kv7.3, Kv7.4, or Kv7.5.

6. The method of claim 5, wherein the method is selective for enhancing the opening of one or more of Kv7.2, Kv7.3, Kv7.4, or Kv7.5 over Kv7.1.

7. The method of claim 4, wherein the method comprises opening of the Kv7.2/Kv7.3 (KCNQ2/3) potassium channel.

8. The method of claim 1, wherein the depressive disorder is major depressive disorder (MDD), disruptive mood dysregulation disorder, persistent depressive disorder, bipolar spectrum disorder, postpartum depression, premenstrual dysphoric disorder (PMDD), season affective disorder (SAD), atypical depression, treatment-resistant depression (TRD), depression associated with agitation or anxiety, adjustment disorder with depressed mood, prolonged depressive reaction, or a combinatioin thereof.

9. The method of claim 8, wherein the depressive disorder is major depressive disorder (MDD).

10. The method of claim 1, wherein Compound A is administered a dose of 2 to 200 mg to the human.

11. The method of claim 10, wherein Compound A is administered at a dose of 5 to 50 mg to the human.

12. The method of claim 10, wherein Compound A is administered at a dose of 10, 15, 20, or 25 mg to the human.

13. The method of claim 1, wherein Compound A is administered at a dose of at least 20 mg to the human.

14. The method of claim 1, wherein Compound A is administered at a dose of 25 mg per day to the human.

15. The method of claim 1, wherein Compound A is administered at a dose of 30 mg per day to the human.

16. The method of claim 1, wherein Compound A is administered at a dose of 20-150 mg per day to the human.

17. The method of claim 1, wherein Compound A is administered at a dose of 100 mg per day to the human.

18. The method of claim 1, wherein Compound A is administered at a dose of 0.05-2.0 mg/kg to the human.

19. The method of claim 18, wherein Compound A is administered at a dose of 0.1-1.0 mg/kg to the human.

20. The method of claim 19, wherein Compound A is administered at a dose of 0.2-0.5 mg/kg to the human.

21. The method of claim 1, wherein Compound A is orally administered as a single dose of 10-30 mg per day.

* * * * *

UNITED STATES PATENT AND TRADEMARK OFFICE
CERTIFICATE OF CORRECTION

PATENT NO. : 12,178,811 B2
APPLICATION NO. : 17/093183
DATED : December 31, 2024
INVENTOR(S) : Cynthia Louise Harden et al.

Page 1 of 1

It is certified that error appears in the above-identified patent and that said Letters Patent is hereby corrected as shown below:

On the Title Page

Item (57), Lines 4-6, please replace: "N-[4-(6-fluoro-3,4-dihydro-1H-isoquinolin-2-yl)-2,6-dimethylphenyl]-3,3-dimethylbutanamide" with --*N*-[4-(6-fluoro-3,4-dihydro-1*H*-isoquinolin-2-yl)-2,6-dimethylphenyl]-3,3-dimethylbutanamide--

In the Claims

In Claim 4, at Column 20, Line 65, please replace: "humam" with --human--

In Claim 6, at Column 21, Line 3, please replace: "Kv7.5over" with --Kv7.5 over--

In Claim 8, at Column 21, Line 10, please replace: "season" with --seasonal--

In Claim 8, at Column 21, Line 14, please replace: "combinatioin" with --combination--

In Claim 10, at Column 21, Line 18, please replace: "administered a dose of" with --administered at a dose of--

Signed and Sealed this
Eighth Day of April, 2025

Coke Morgan Stewart
*Acting Director of the United States Patent and Trademark Office*